(12) United States Patent
Lee et al.

(10) Patent No.: US 11,130,993 B2
(45) Date of Patent: Sep. 28, 2021

(54) LED DRIVEN PLASMONIC HEATING APPARATUS FOR NUCLEIC ACIDS AMPLIFICATION

(71) Applicant: THE REGENTS OF THE UNIVERSITY OF CALIFORNIA, Oakland, CA (US)

(72) Inventors: Luke P. Lee, Orinda, CA (US); Jun Ho Son, Albany, CA (US); Byungrae Cho, Albany, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/649,328

(22) Filed: Jul. 13, 2017

(65) Prior Publication Data
US 2018/0080064 A1 Mar. 22, 2018

Related U.S. Application Data

(63) Continuation of application No. PCT/US2016/013732, filed on Jan. 15, 2016.

(60) Provisional application No. 62/104,574, filed on Jan. 16, 2015.

(51) Int. Cl.
*B01L 3/00* (2006.01)
*C12Q 1/686* (2018.01)
*B01L 7/00* (2006.01)

(52) U.S. Cl.
CPC .......... *C12Q 1/686* (2013.01); *B01L 3/50851* (2013.01); *B01L 7/52* (2013.01); *B01L 2200/147* (2013.01); *B01L 2300/0829* (2013.01); *B01L 2300/0896* (2013.01); *B01L 2300/168* (2013.01); *B01L 2300/1861* (2013.01)

(58) Field of Classification Search
None
See application file for complete search history.

(56) References Cited

U.S. PATENT DOCUMENTS

| 8,049,163 B1* | 11/2011 | Granneman | G01J 5/522 250/252.1 |
| 9,901,923 B2* | 2/2018 | Lee | G01N 15/0227 |
| 2001/0029017 A1* | 10/2001 | Yasuda | B01L 3/5027 435/6.11 |

(Continued)

FOREIGN PATENT DOCUMENTS

| WO | 2013113910 A1 | 8/2013 |
| WO | 2014140596 A1 | 9/2014 |

OTHER PUBLICATIONS

Korean Intellectual Property Office (KIPO), International Search Report and Written Opinion dated Apr. 29, 2016, counterpart PCT International Application No. PCT/US2016/013732, pp. 1-19, with claims searched, pp. 20-24.

(Continued)

*Primary Examiner* — Robert T. Crow
(74) *Attorney, Agent, or Firm* — O'Banion & Ritchey LLP; John P. O'Banion

(57) ABSTRACT

Systems and methods for plasmonic heating by combined use of thin plasmonic film-based 2D and 3D structures and a light-emitting diode (LED) for nucleic acids amplification through fast thermal cycling of polymerase chain reaction (PCR) are described.

24 Claims, 22 Drawing Sheets

(56) References Cited

U.S. PATENT DOCUMENTS

| | | | | |
|---|---|---|---|---|
| 2003/0219754 | A1* | 11/2003 | Oleksy | C12Q 1/6818 |
| | | | | 435/6.11 |
| 2004/0029258 | A1* | 2/2004 | Heaney | B01L 3/5025 |
| | | | | 435/287.2 |
| 2004/0241691 | A1* | 12/2004 | Bachi | B01L 7/52 |
| | | | | 435/6.11 |
| 2005/0009070 | A1* | 1/2005 | Arciniegas | B01L 9/06 |
| | | | | 435/6.11 |
| 2005/0287661 | A1* | 12/2005 | Landers | B01L 3/5027 |
| | | | | 435/303.1 |
| 2008/0245430 | A1* | 10/2008 | Adleman | B01L 3/50273 |
| | | | | 137/827 |
| 2009/0075843 | A1* | 3/2009 | Jiang | C40B 60/12 |
| | | | | 506/39 |
| 2009/0261086 | A1* | 10/2009 | Beer | H05B 3/0033 |
| | | | | 219/383 |
| 2010/0243078 | A1* | 9/2010 | Yoo | F16K 99/0001 |
| | | | | 137/468 |
| 2011/0008785 | A1* | 1/2011 | Tan | B01L 7/52 |
| | | | | 435/6.12 |
| 2012/0064534 | A1* | 3/2012 | Pipper | B03C 3/017 |
| | | | | 435/6.12 |
| 2012/0107952 | A1* | 5/2012 | Geddes | B82Y 15/00 |
| | | | | 436/501 |
| 2013/0243947 | A1 | 9/2013 | Yang | |
| 2014/0170664 | A1 | 6/2014 | Roche | |

OTHER PUBLICATIONS

Neuzil, Pavel et al., "Ultra fast miniaturized real-time PCR: 40 cycles in less than six minutes", Nucleid Acids Research, 2006, vol. 34, No. 11, pp. 1-9.

Son, Jun Ho et al., "Ultrafast photonic PCR", Light: Science & Applications (2015) 4, pp. 1-7, supplementary information, pp. 8-14.

Kim, Hanyoup et al., "Petri dish PCR: laser-heated reactions in nanoliter droplet arrays", Lab Chip 2009, 9, 1230-1235, Jan. 19, 2009.

Miralles, Vincent. et al., "A review on heating and temperature control in microfluidic systems: techniques and applications", Diagnostics 2013, 3, 33-67, Jan. 15, 2013.

Kim, Hanyoup et al., "Nanodroplet real-time PCR system with laser assisted heating", Optics Express, vol. 17, No. 1, Jan. 5, 2009, pp. 218-227.

Roche, Philip J. R. et al., "Demonstration of a plasmonic thermocycler for the amplification of human androgen receptor DNA", Analyst, 2012, 137, 4475-4481, Jul. 17, 2012.

European Patent Office (EPO), Communication (extended European searech report) dated May 24, 2018, related European patent application No. 16738021.1, pp. 1-6, claims searched, pp. 7-9.

European Patent Office (EPO), Communication pursuant to Article 93 (EPC) dated Feb. 28, 2019, related European patent application No. 16738021.1, pp. 1-5, claims examined, pp. 6-8.

European Patent Office (EPO), Communication pursuant to Article 94(3) (EPC) dated Nov. 26, 2019, related European patent application No. 16738021.1, pp. 1-4, claims examined, pp. 5-7.

Korean Intellectual Property Office (KIPO), Notification of Reason for Refusal dated Jun. 16, 2020, related Korean patent application No. 10-2017-7022610, pp. 1-8, English-language translation, pp. 9-16, claims examined, pp. 17-21.

Corie, Michael et al., "Plasmonic heating of gold nanoparticles and its exploitation", Proceedings of SPIE, Smart Structures, Devices and Systems II, Dec. 13-15, 2004, Sydney Australia, vol. 5649, pp. 565-573.

\* cited by examiner

LED DRIVEN PLASMONIC HEATING APPARATUS FOR NUCLEIC ACIDS AMPLIFICATION

CROSS-REFERENCE TO RELATED APPLICATIONS

This application is a 35 U.S.C. § 111(a) continuation of PCT international application number PCT/US2016/013732 filed on Jan. 15, 2016, incorporated herein by reference in its entirety, which claims priority to, and the benefit of, U.S. provisional patent application Ser. No. 62/104,574 filed on Jan. 16, 2015, incorporated herein by reference in its entirety. Priority is claimed to each of the foregoing applications.

The above-referenced PCT international application was published as PCT International Publication No. WO 2016/115542 on Jul. 21, 2016, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to systems and methods for polymerase chain reaction (PCR) diagnostics, and more particularly to plasmonic heating systems and methods for fast/ultrafast PCR.

2. Background Discussion

After its initial introduction in 1983, polymerase chain reaction (PCR) has become an essential technique in the field of clinical laboratories, agricultural science, environmental science, and forensic science. PCR uses thermal cycling, or repeated temperature changes between 2 or 3 discrete temperatures to amplify specific nucleic acid target sequences. To achieve such thermal cycling, conventional bench-top thermal cyclers generally use the metal heating block powered by Peltier elements. While commercial PCR systems are improving heating and cooling rates to reduce amplification time, they are still relatively time-consuming (typically requiring an hour or more per amplification). This can be attributed to the larger thermal capacitance of a system that requires uniform heating 96- or 384-well plastic PCR plates and reaction volumes of several tens of microliters per well.

Since fast/ultrafast PCR is highly desirable for applications such as timely diagnosis of infectious diseases, cardiac diseases, cancer, neurological disorder diseases, and rapid biowarfare and pathogen identification at the point-of-care (POC) level, many academic and industrial groups have been improving PCR systems. However, existing systems are not suitable for POC testing due to high power consumption, heavy weight require a complicated fabrication process, prone to human error, require expensive lasers and detection systems, or have reliability issues.

Accordingly, an object of the present description is a fast/ultrafast PCR system that is portable, robust, simple, easy to use and characterized by low power consumption through miniaturization and integration.

BRIEF SUMMARY

The present description is directed to systems and methods for nucleic acid amplification and quantification via polymerase chain reaction (PCR) for clinical laboratories, precision medicine, personalized medicine, agricultural science, forensic science, and environmental science. Ultrafast multiplex PCR, characterized by low power consumption, compact size and simple operation, is ideal for timely diagnosis at the point-of-care (POC).

One aspect is an ultrafast photonic PCR method using plasmonic photothermal light-to-heat conversion via photon-electron-phonon coupling. An efficient photonic heat converter is disclosed, using a thin gold (Au) film for its plasmon-assisted high optical absorption (~65% at 450 nm, peak wavelength of heat source LEDs). The plasmon-excited Au film is capable of rapidly heating the surrounding solution to over 150° C. within 3 min. Using this method, ultrafast thermal cycling (e.g. 30 cycles; heating and cooling rate of 12.79±0.93° C. sec$^{-1}$ and 6.6±0.29° C. sec$^{-1}$, respectively) from 55° C. (temperature of annealing) to 95° C. (temperature of denaturation) is accomplished within 5 minutes. Using photonic PCR thermal cycles, we demonstrate here successful nucleic acid (λ-DNA) amplification. Our simple, robust and low cost-approach to ultrafast PCR using an efficient photonic-based heating procedure could be generally integrated into a variety of devices or procedures, including on-chip thermal lysis and heating for isothermal amplifications.

Thin Au films with nanometer sized grain prepared by electron beam evaporation are characterized to enhance light absorption through surface plasmon resonance, leading to fast plasmonic heating of thin Au film. Low cost (<$5) LED can effectively increase temperature of liquid up to 140° C. by focusing light with low cost lens (<$1). The maximum ramp rate is up to 7° C./sec and temperature stability at 50° C. and 90° C. are ±0.5° C. and ±0.7° C., respectively. Nucleic acids amplifications through fast thermal cycling (from 50° C. to 90° C., 40 cycles for 19 min) for PCR are successfully demonstrated using a LED driven plasmonic heating of thin Au films. With this invention, we can obtain simple, portable PCR thermal cycler with extremely low cost and power consumption for point-of-care diagnostics.

The technology could be easily used for fast thermal cycler for nucleic acids detection using PCR and/or isothermal amplification including LAMP and RPA. Fast thermal cycler for PCR nucleic acids detection would be the best ways to utilize the disclosed invention.

In general, the invention will be used for fast thermal cycling for nucleic acids amplifications using polymerase chain reaction (PCR), loop-mediated isothermal amplification (LAMP), and recombinase polymerase amplification (RPA) in point-of-care testing for human, animal healthcare or environmental.

The most distinctive advantage is to obtain low cost (LEDs <$5, focus lens <$1) and low power consumption (LEDs <3 W) thermal cycler with simple plasmonic heater fabrication (complicated patterning process or expensive gold nanoparticles are not required). Furthermore, its simplicity and easy system level integration for point-of-care nucleic acids testing are other advantages.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

Figure 4A:
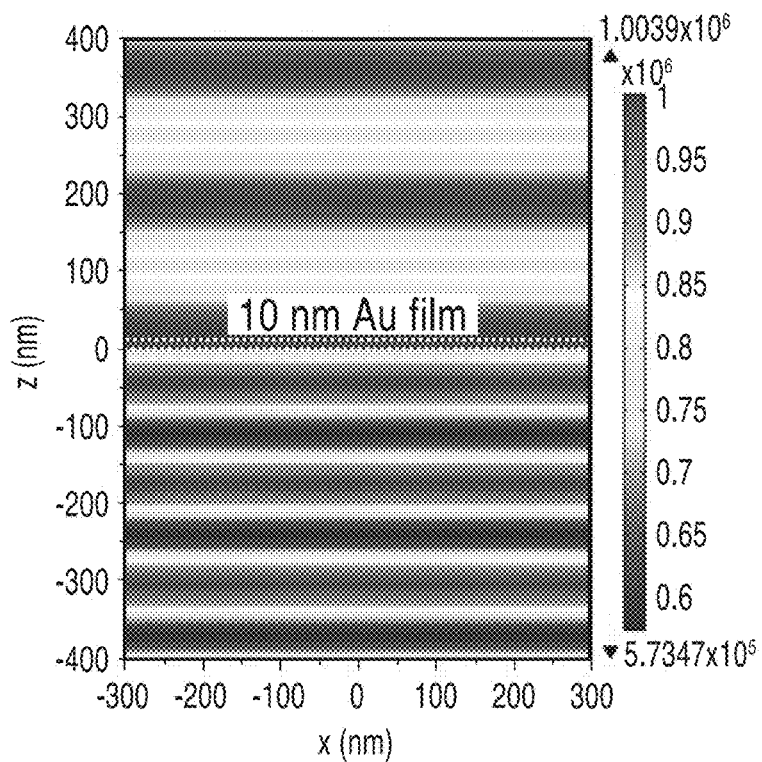
Figure 4B:
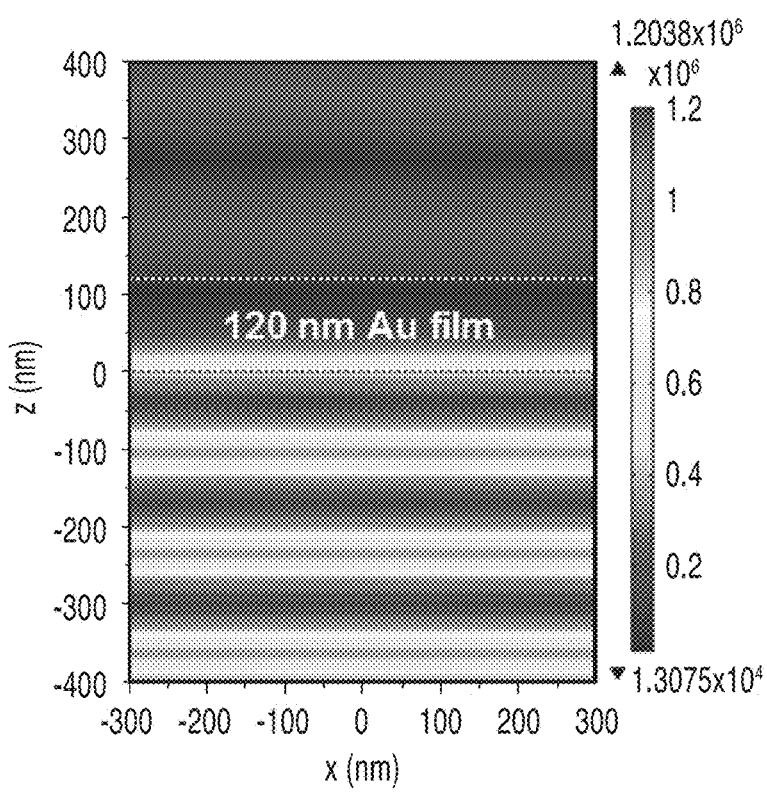
Figure 4C:
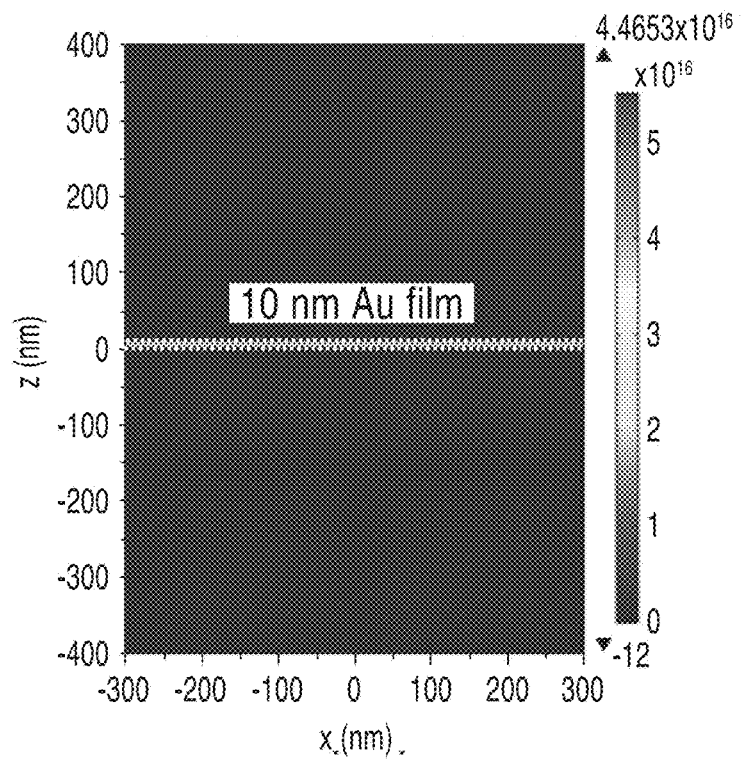
Figure 4D:
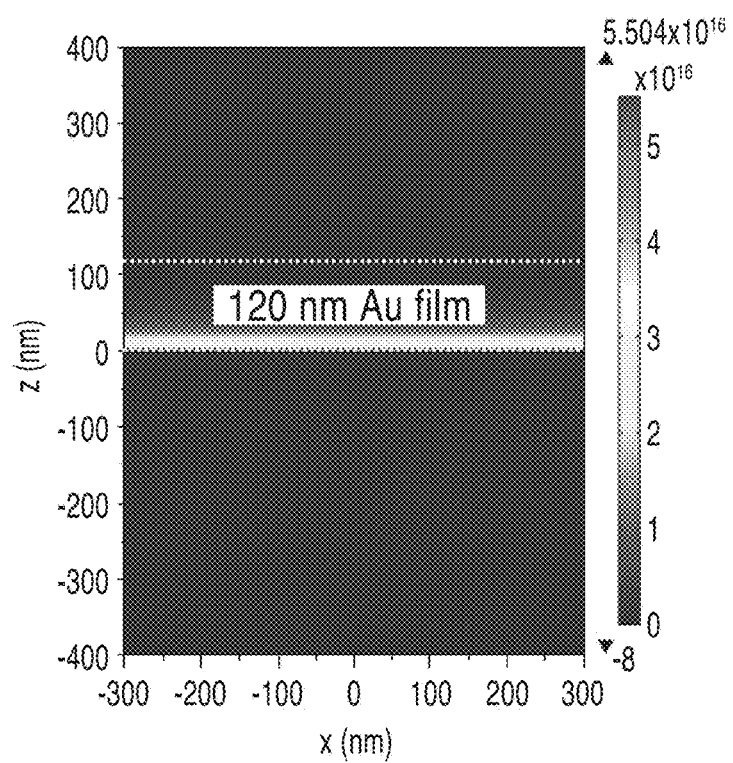
Figure 4E:
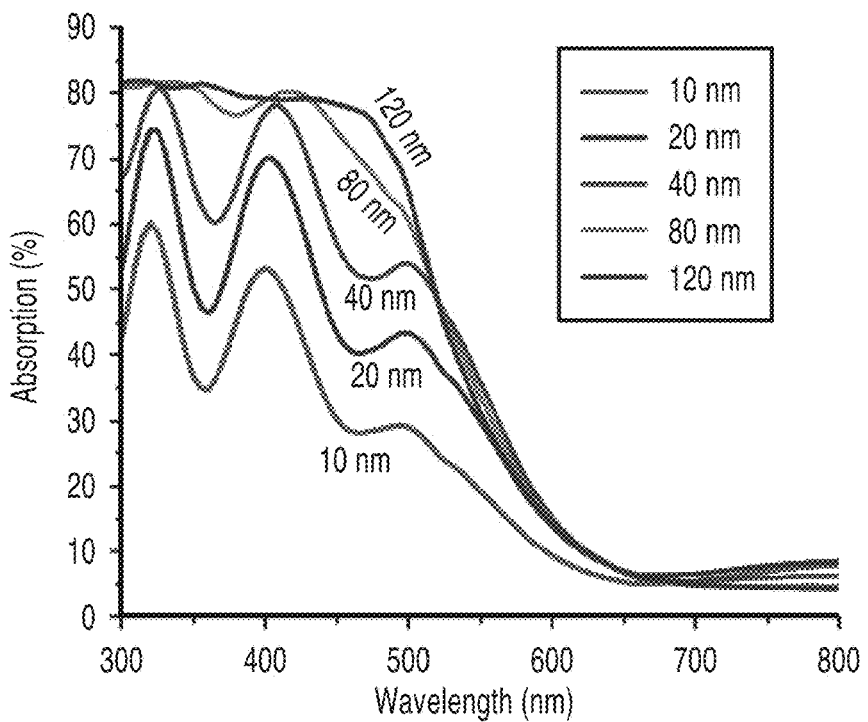
Figure 4F:
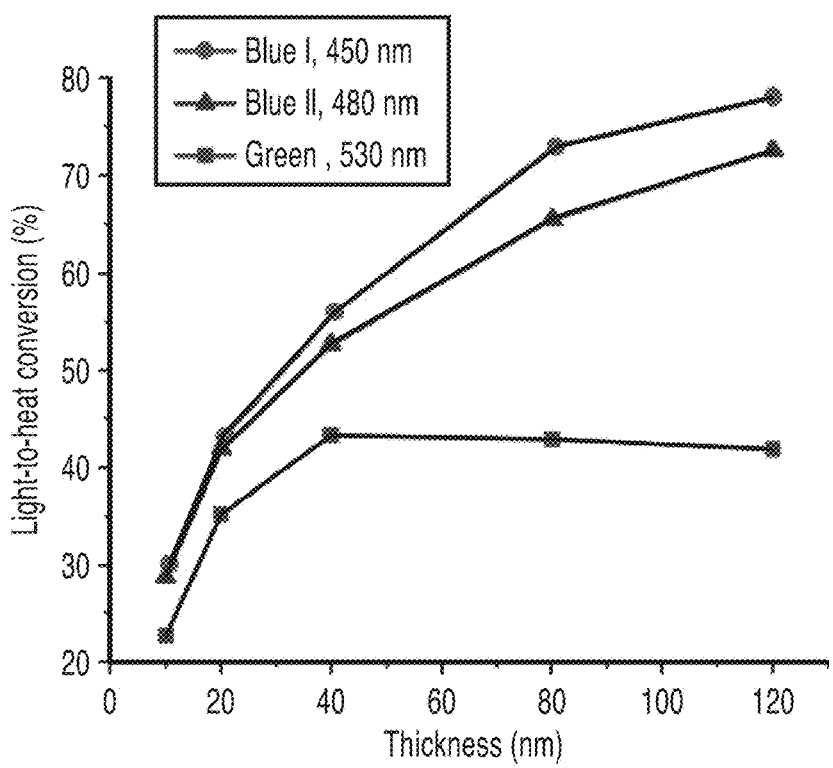

FIG. 4A through FIG. 4F show simulation for heat generation of thin Au films of the present description with electromagnetic radiation. FIG. 4A and FIG. 4B show images for electromagnetic field on 10 nm and 120 nm thick Au films on PMMA substrate, respectively. FIG. 4C and FIG. 4D show images for resistive heat distributions on 10 nm and 120 nm thick Au films on PMMA substrate, respectively. FIG. 4E shows a plot of calculated absorption spectra of the thin Au films with different thickness. FIG. 4F shows a plot of light-to-heat conversion efficiency of the thin Au films averaged over emission wavelength from 3 different colored LEDs as a function of Au films thickness.

FIG. 5A through FIG. 5F show plots of LED driven photothermal heating of thin Au film and PCR thermal cycling.

Figure 6A:
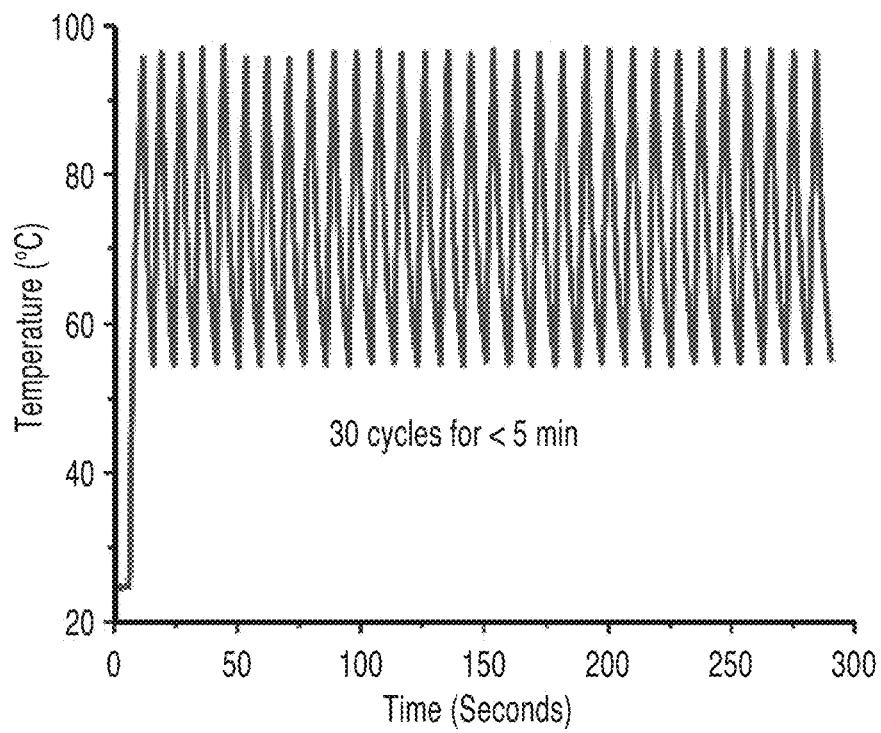

FIG. 6A is a plot of representative temperature profiles of 30 ultrafast photonic PCR thermal cycles from 95° C. (denaturation) to 55° C. (annealing and extension).

Figure 6B:
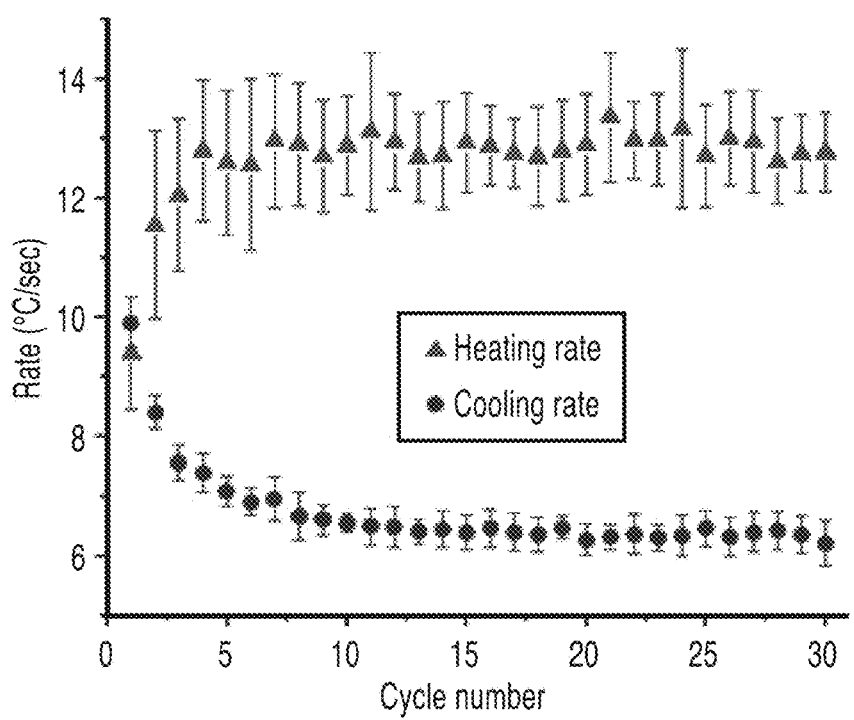

FIG. 6B shows a plot of heating and cooling rates obtained from the ultrafast photonic thermal cycling.

Figure 6C:
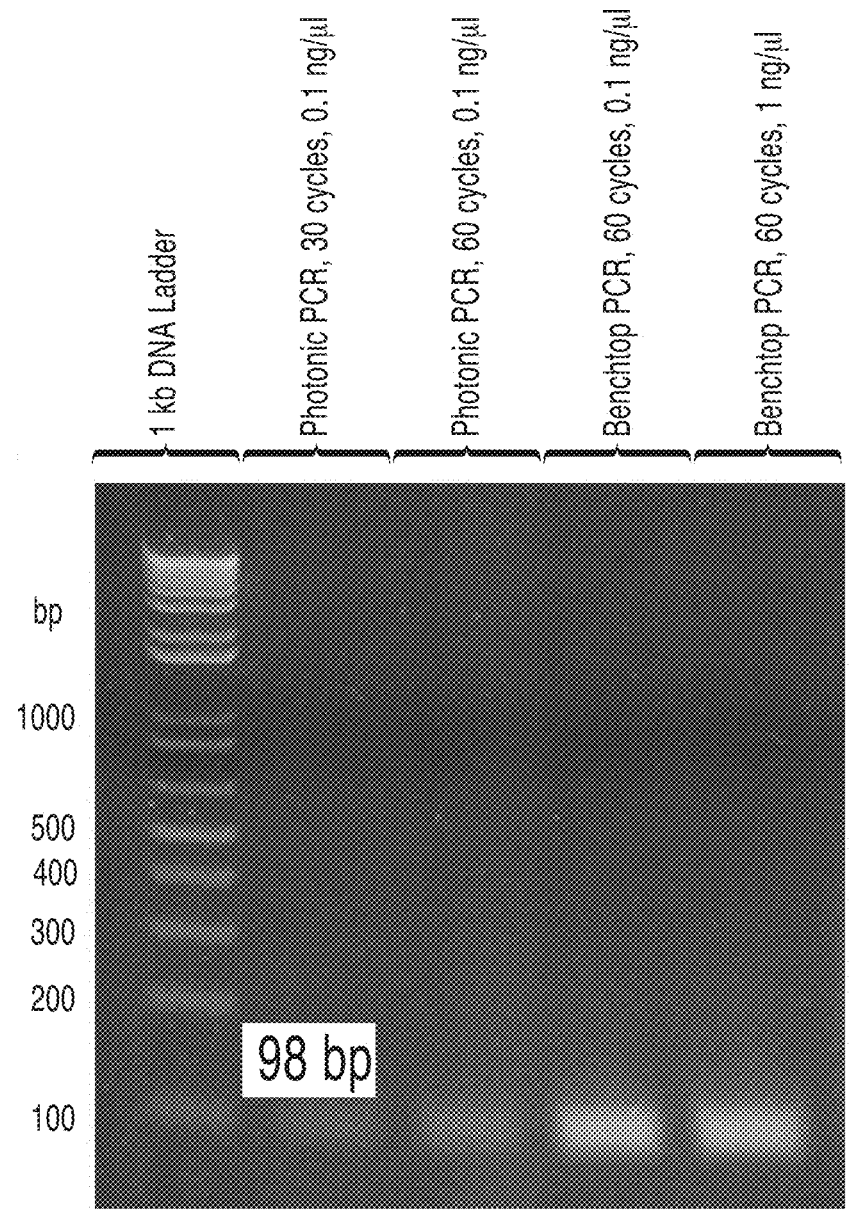

FIG. 6C is an image showing formation of product from the photonic PCR thermal cycler in comparison with bench-top thermal cycler using λ DNA template.

Figure 7:
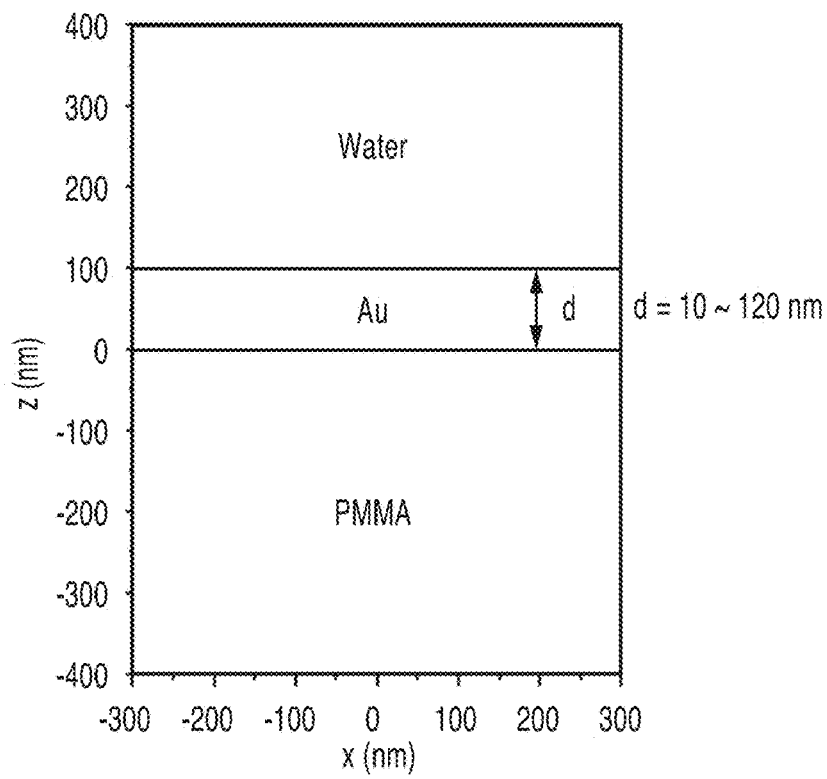

FIG. 7 is a cross-section of representative geometry used for the simulation of electromagnetic field and resistive heat distribution in thin films.

Figure 8:
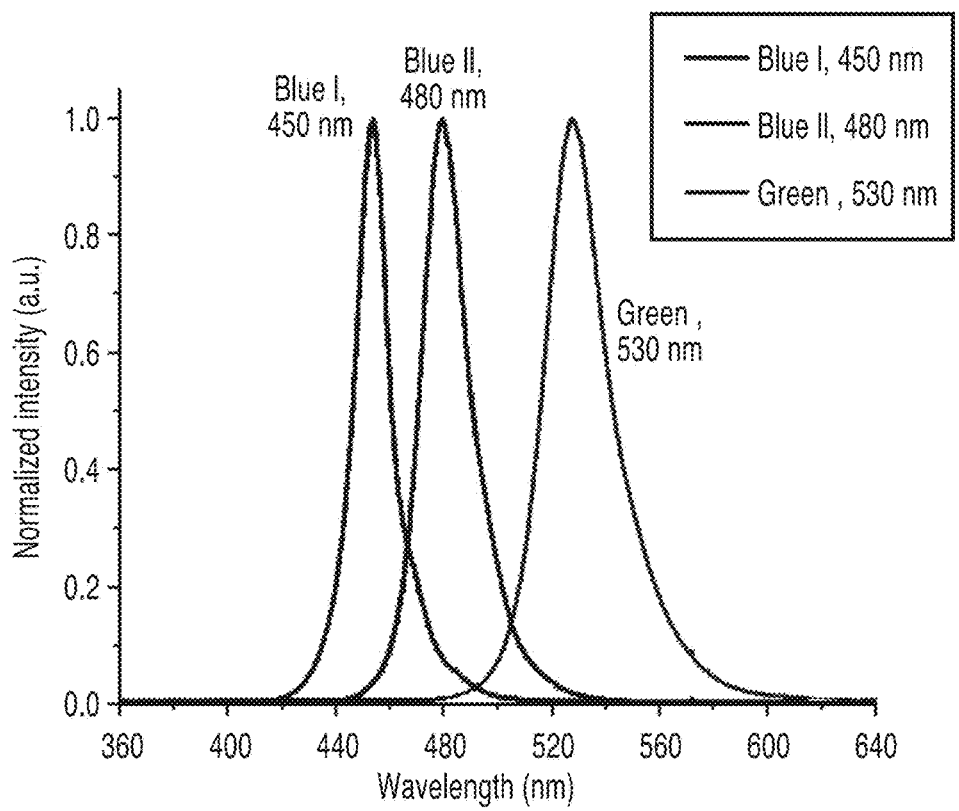

FIG. 8 is a plot of normalized light emission spectra measured from 3 different LEDs with peak wavelengths of 450 nm (Blue I), 480 nm (Blue II) and 530 nm (Green), respectively.

Figure 9A:
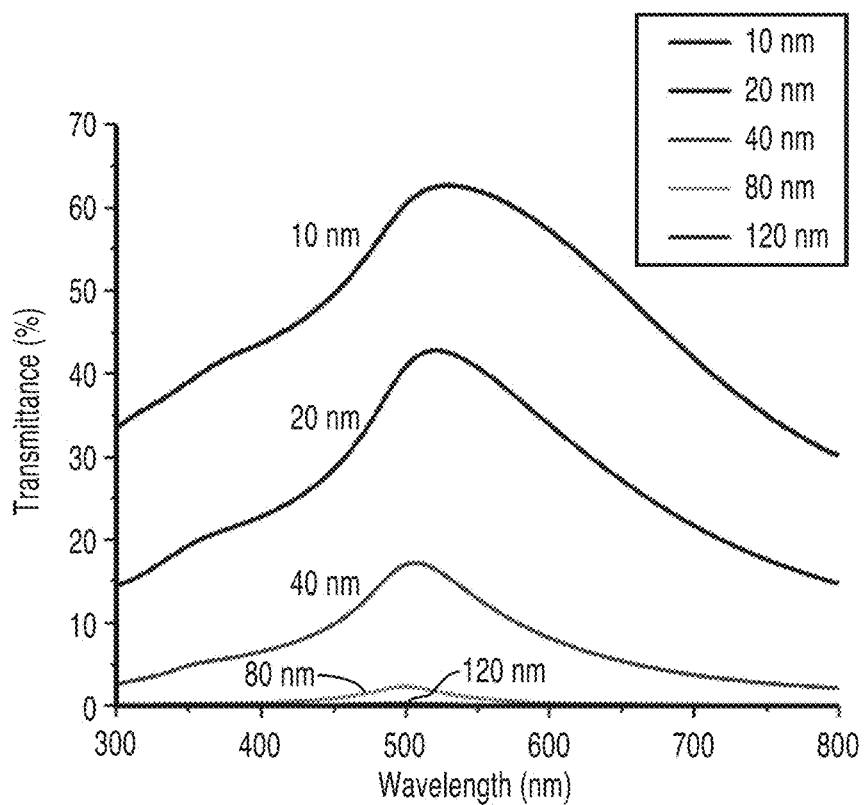
Figure 9B:
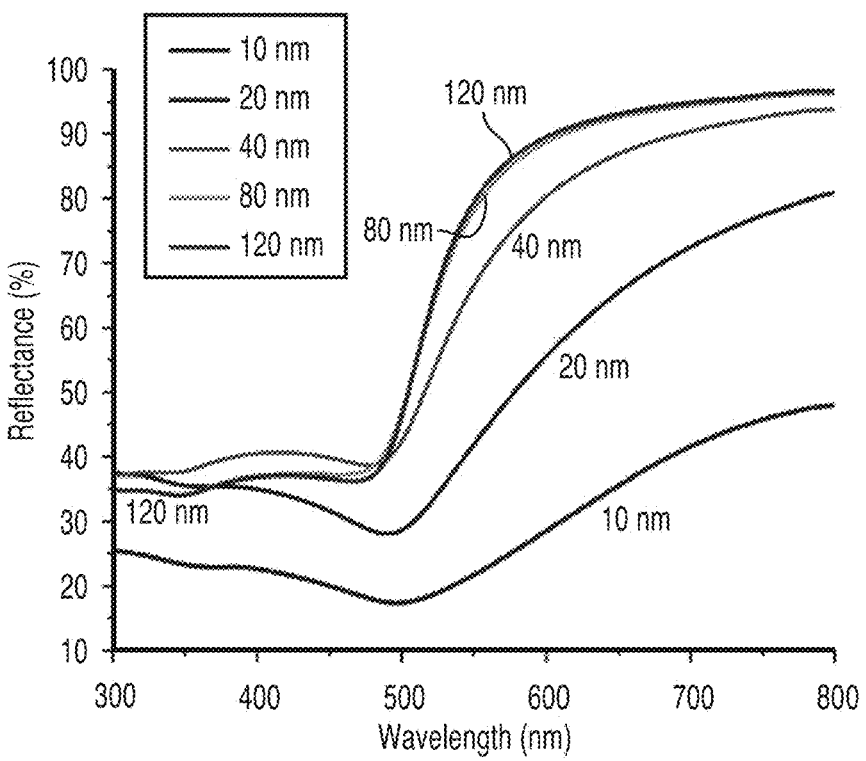

FIG. 9A and FIG. 9B are plots of transmittance and reflectance spectra, respectively, of the thin Au films on PMMA substrate with different thicknesses.

Figure 10:
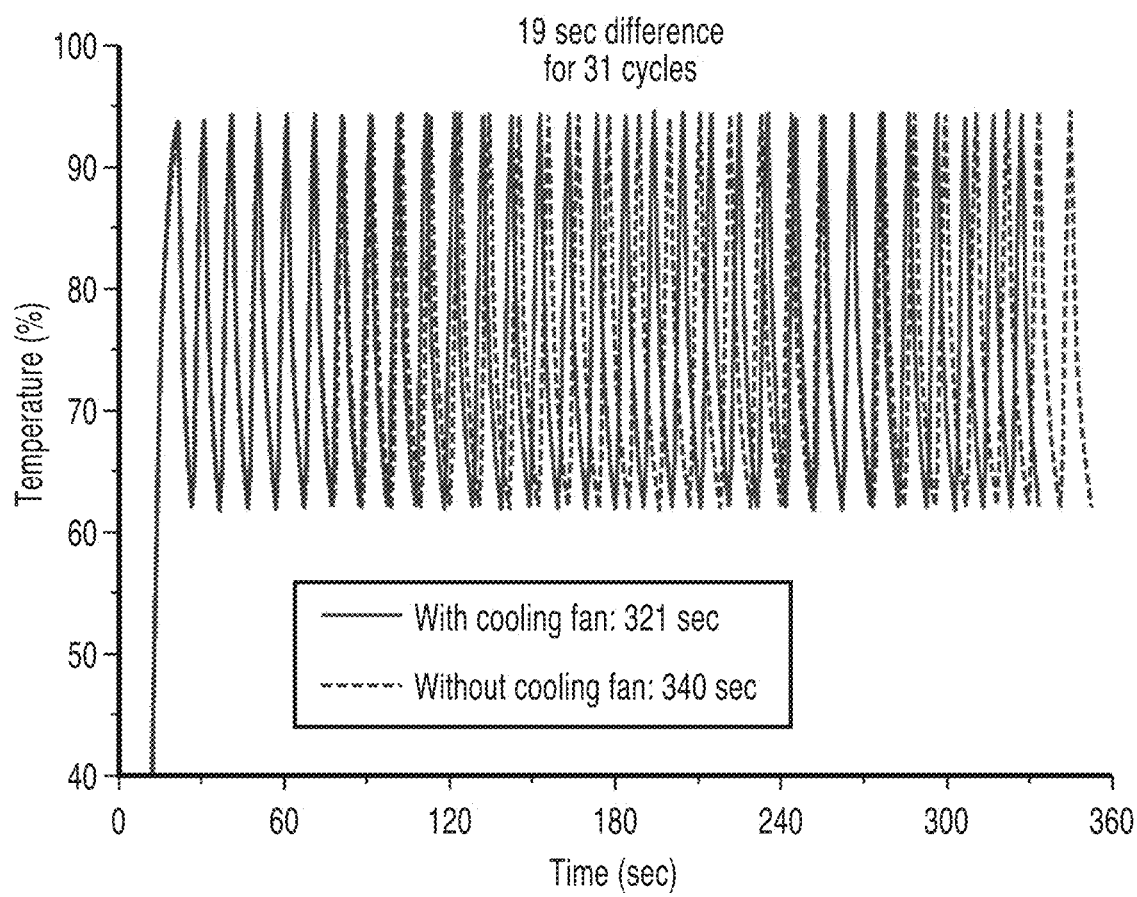

FIG. 10 is a plot comparison of 31 ultrafast thermal cycles from 62° C. to 94° C. with and without cooling fan.

Figure 11:
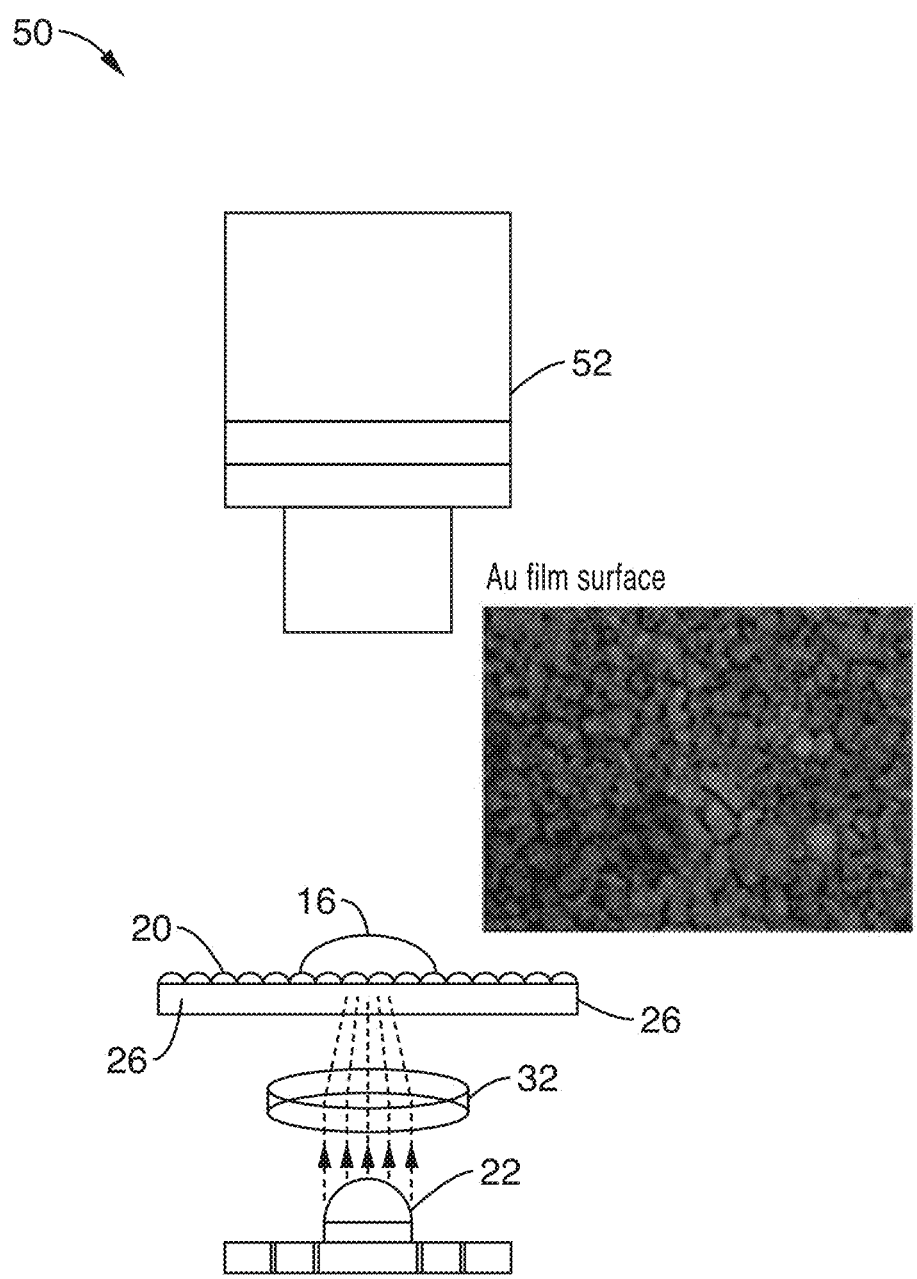

FIG. 11 is a schematic diagram of an experimental set up for LED driven plasmonic heating of thin Au films.

Figure 12:
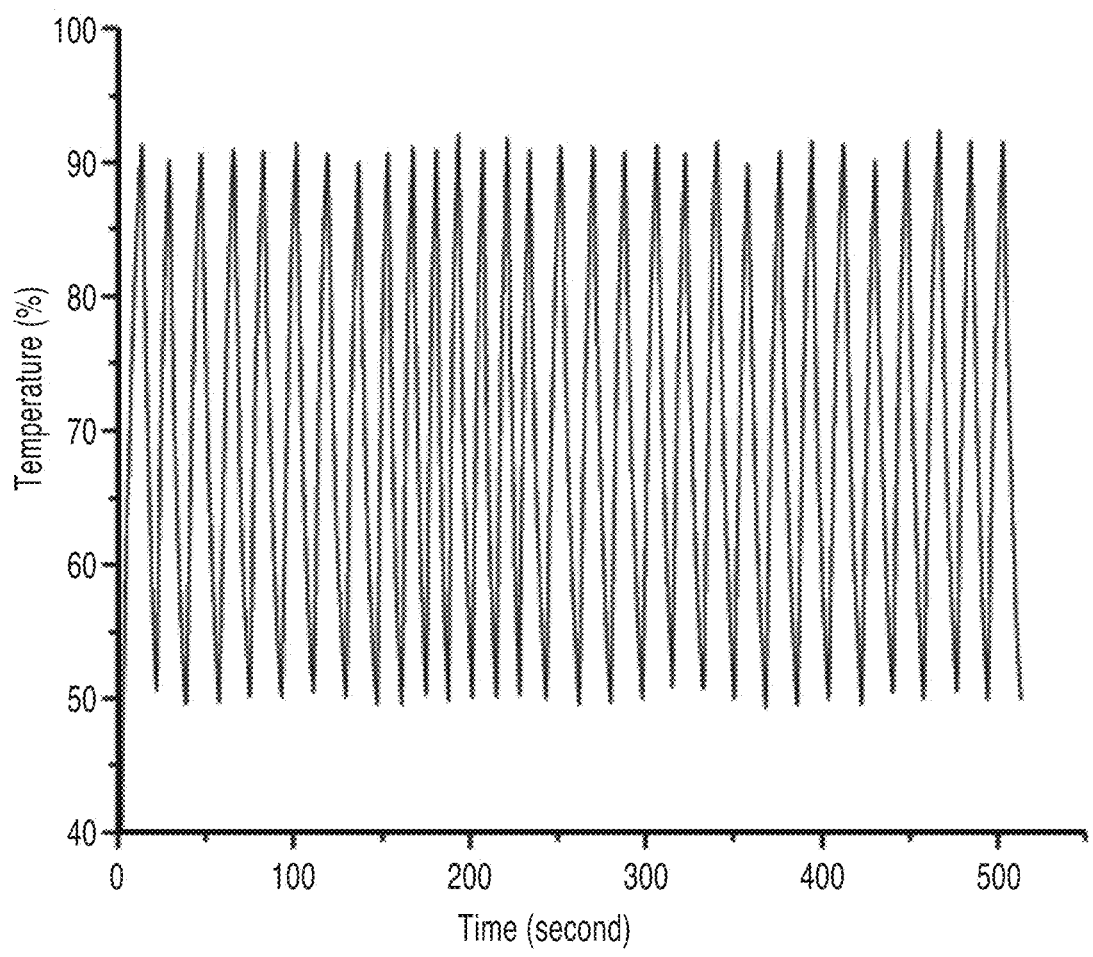

FIG. 12 is a plot showing fast thermal cycling using LED driven plasmonic heating of thin Au films.

Figure 13A:
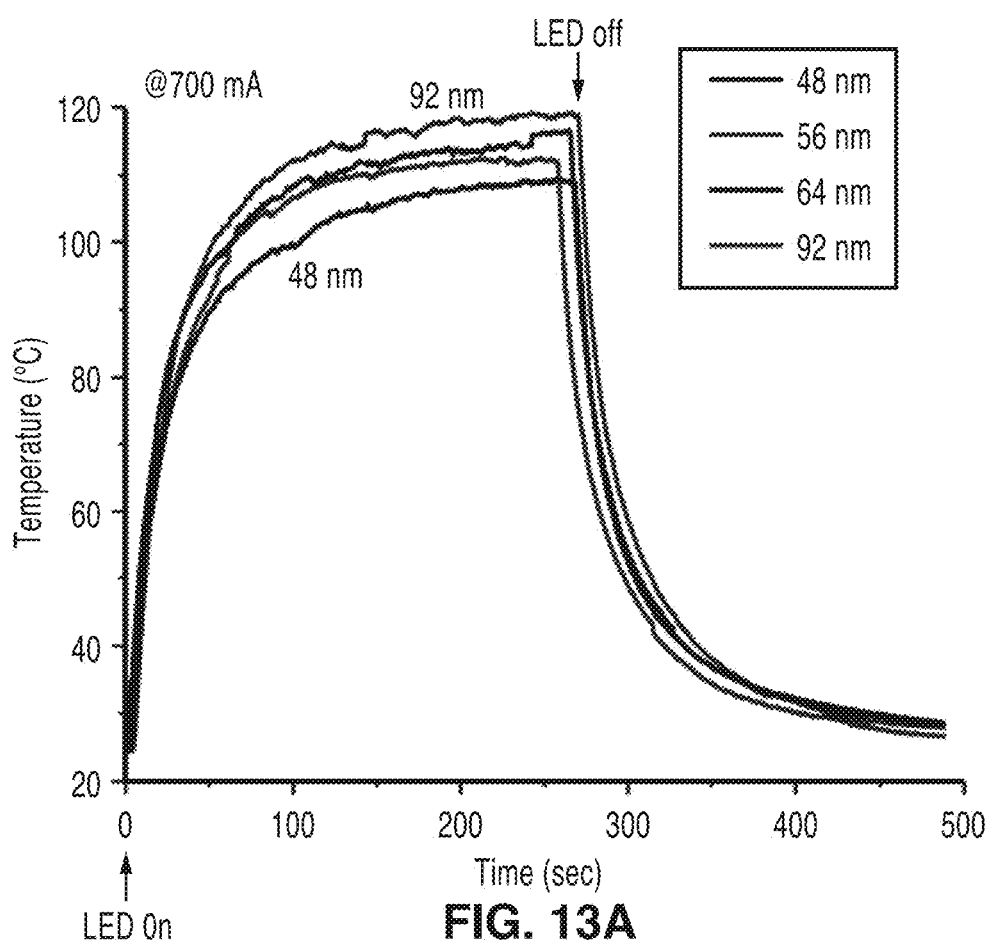

FIG. 13A is a plot showing temperature changes of liquid (glycerol, 5 µL) with different thin Au films thickness. Injection current of LEDs was fixed at 700 mA.

Figure 13B:
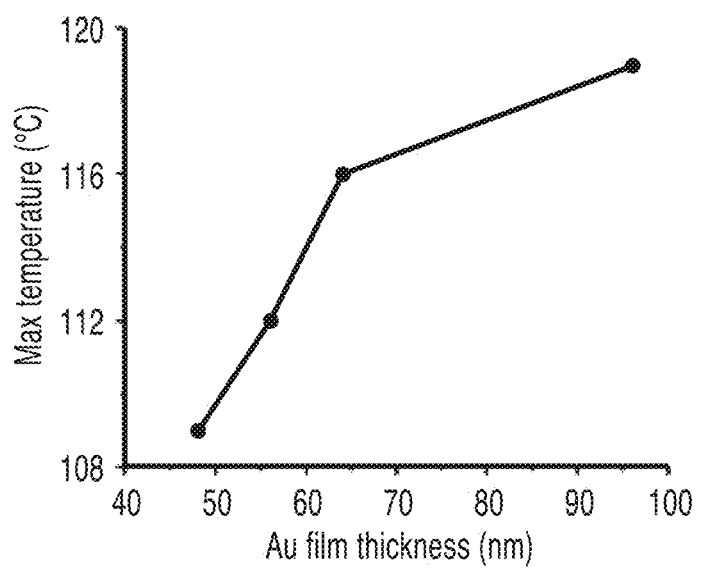

FIG. 13B shows a plot temperature for varying the film 20 thickness.

Figure 13C:
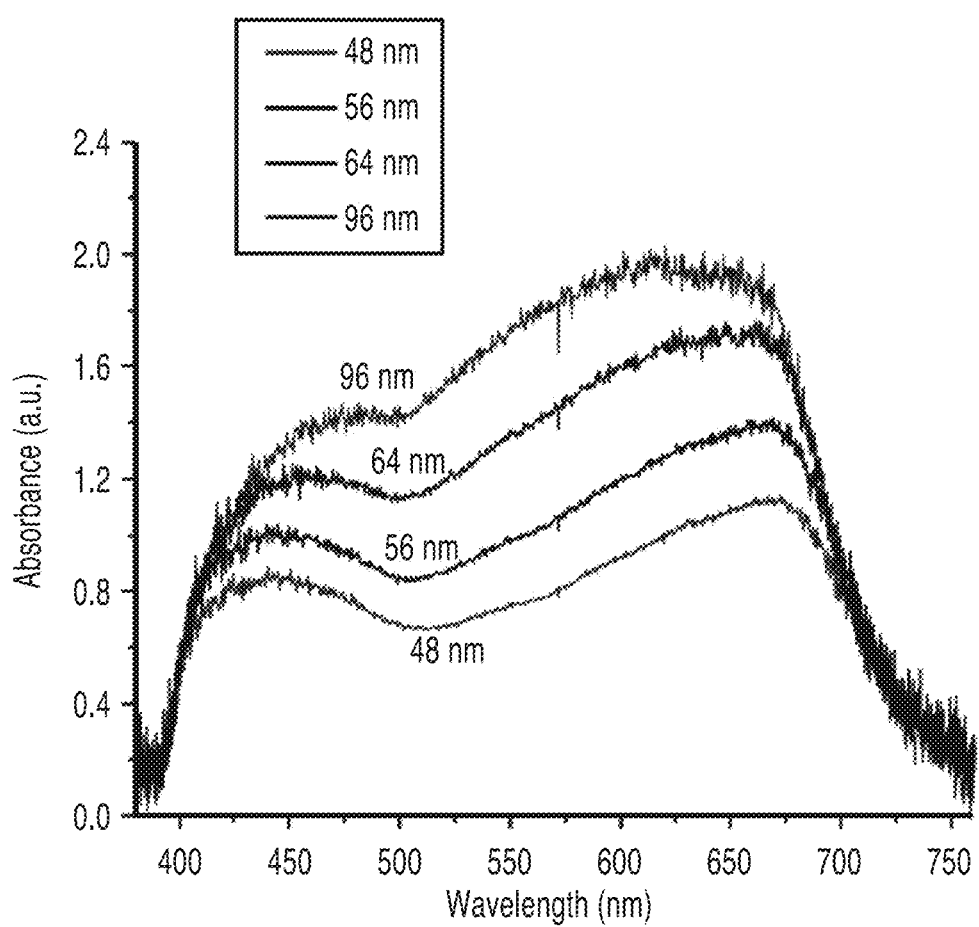

FIG. 13C is a plot showing absorbance changes of thin Au films as a function of wavelength. The inset shows the representative SEM images of thin Au films containing nanometer sized grain.

Figure 13D:
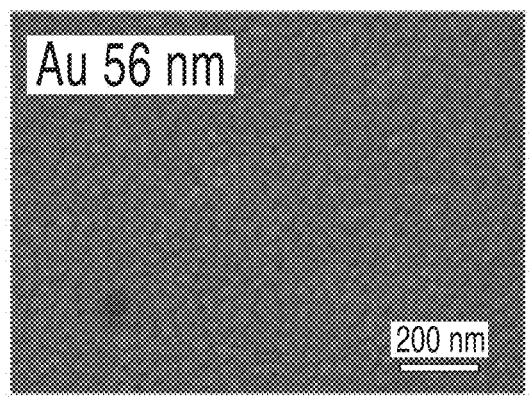
Figure 13E:
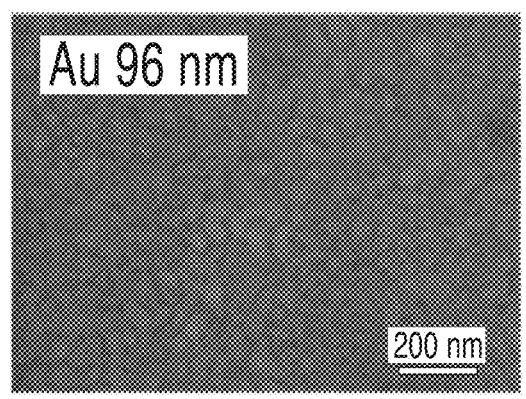

FIG. 13D and FIG. 13E show images of the Au film 20 at 56 nm and 96 nm, respectively.

Figure 14A:
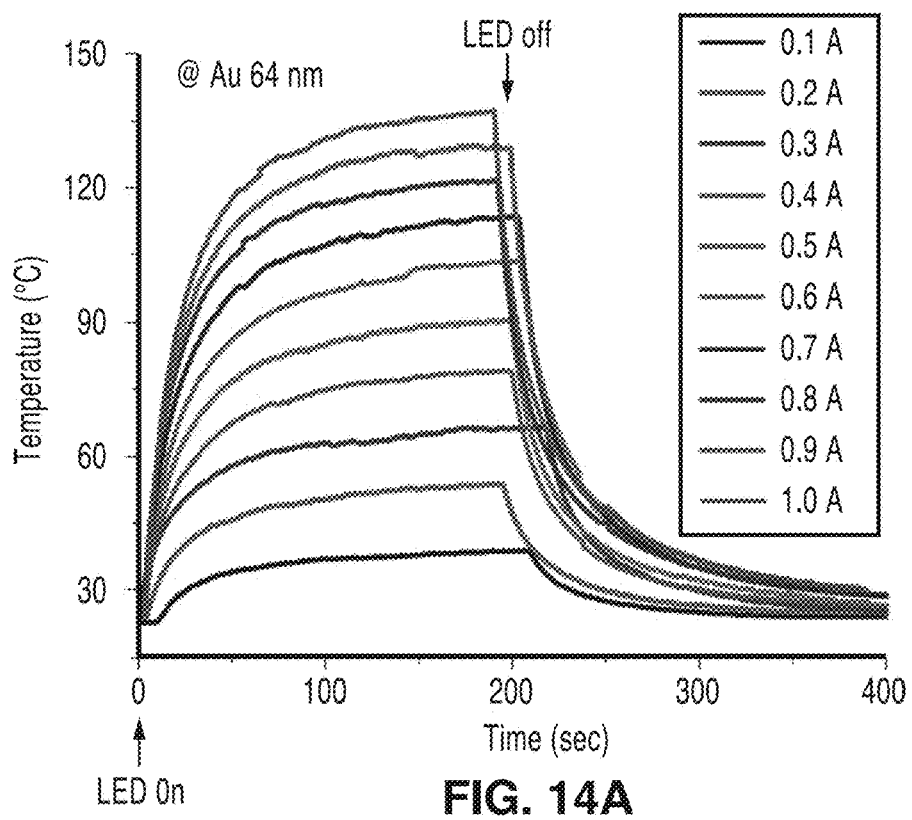

FIG. 14A is a plot of temperature changes of liquid (glycerol, 5 µL) with different injection current of LEDs.

Figure 14B:
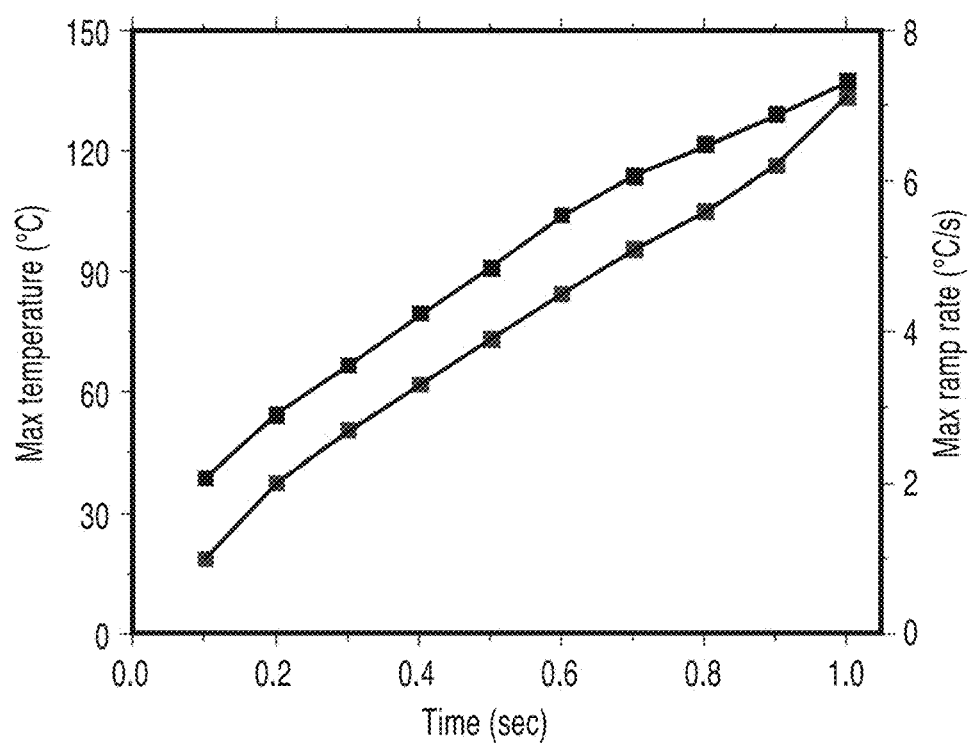

FIG. 14B is a plot illustrating changes of maximum temperature (left axis) and ramp rate (right axis) as a function of injection current.

Figure 15:
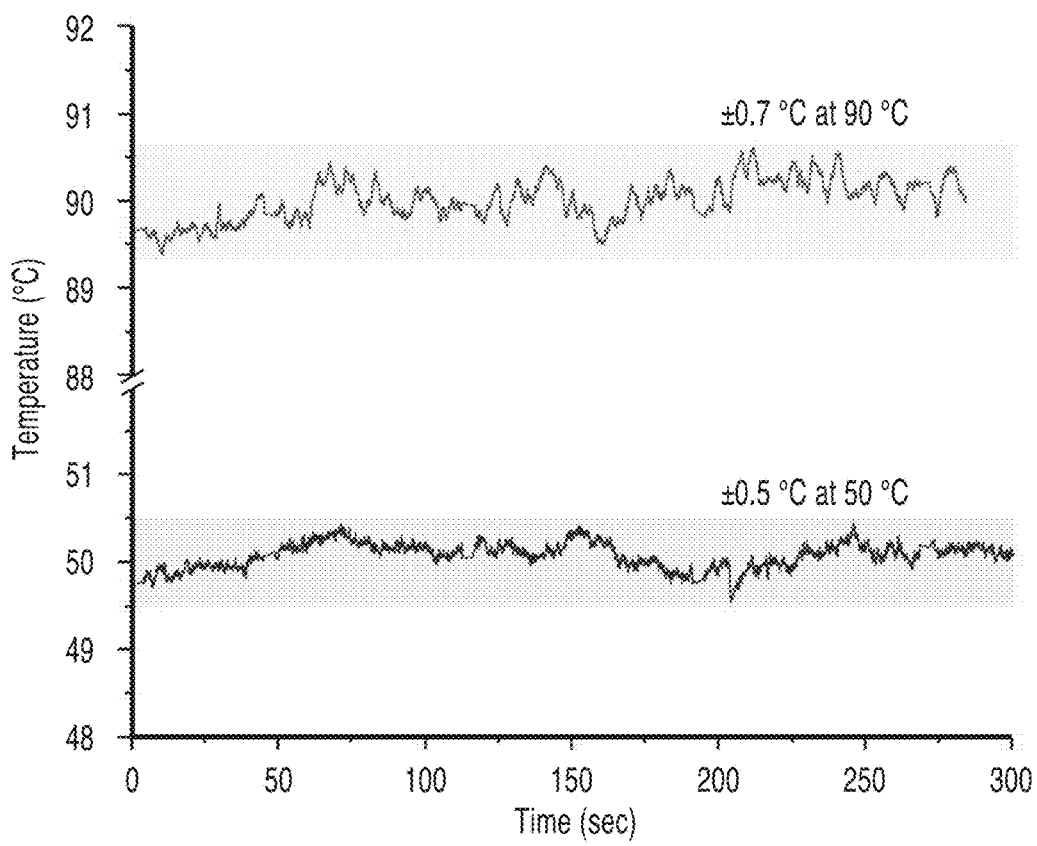

FIG. 15 is a plot of temperature stability of LED driven plasmonic heating of thin Au films at 50° C. and 90° C.

Figure 16:
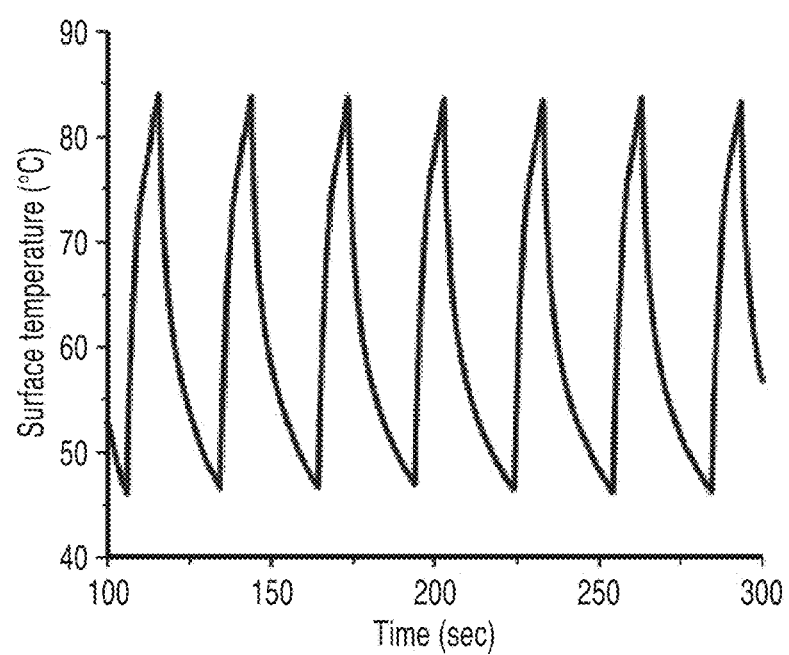

FIG. 16 is a plot of the temperature profiles of thermal cycling measured by IR camera during PCR reaction.

Figure 17:
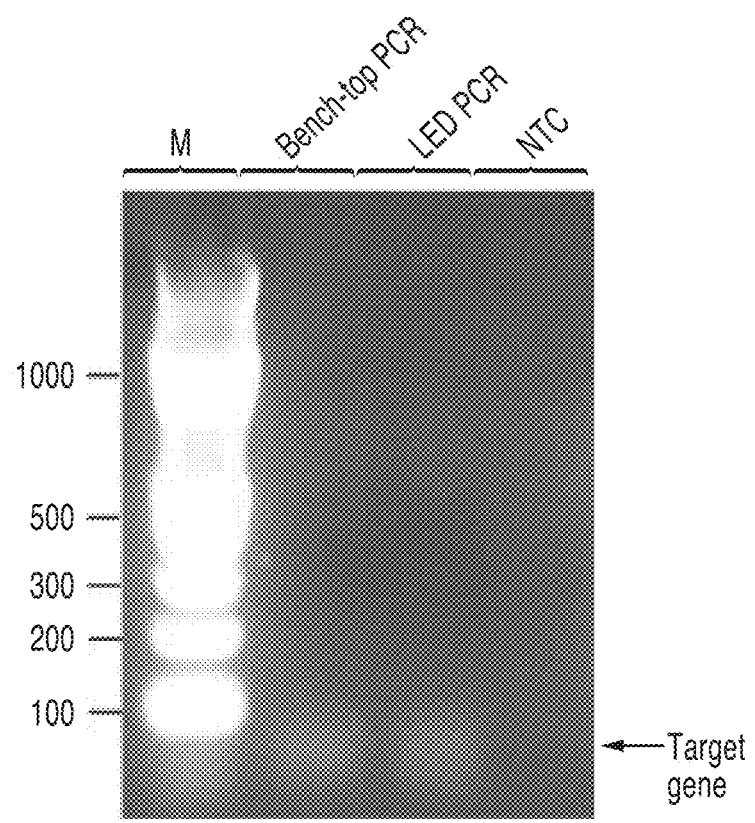

FIG. 17 is a photograph of gel agarose gel demonstrating the formation of product from a plasmonic and bench top thermal cycler.

DETAILED DESCRIPTION

Figure 1:
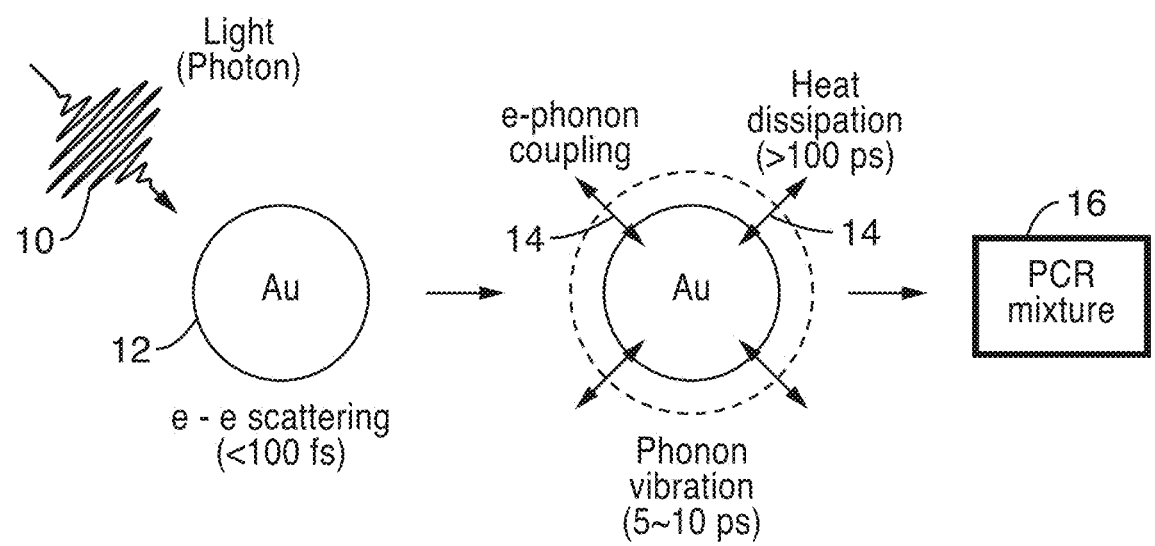
FIG. 1 shows a schematic diagram illustrating the principle of ultrafast photonic PCR in accordance with the technology of the present description.
Figure 2A:
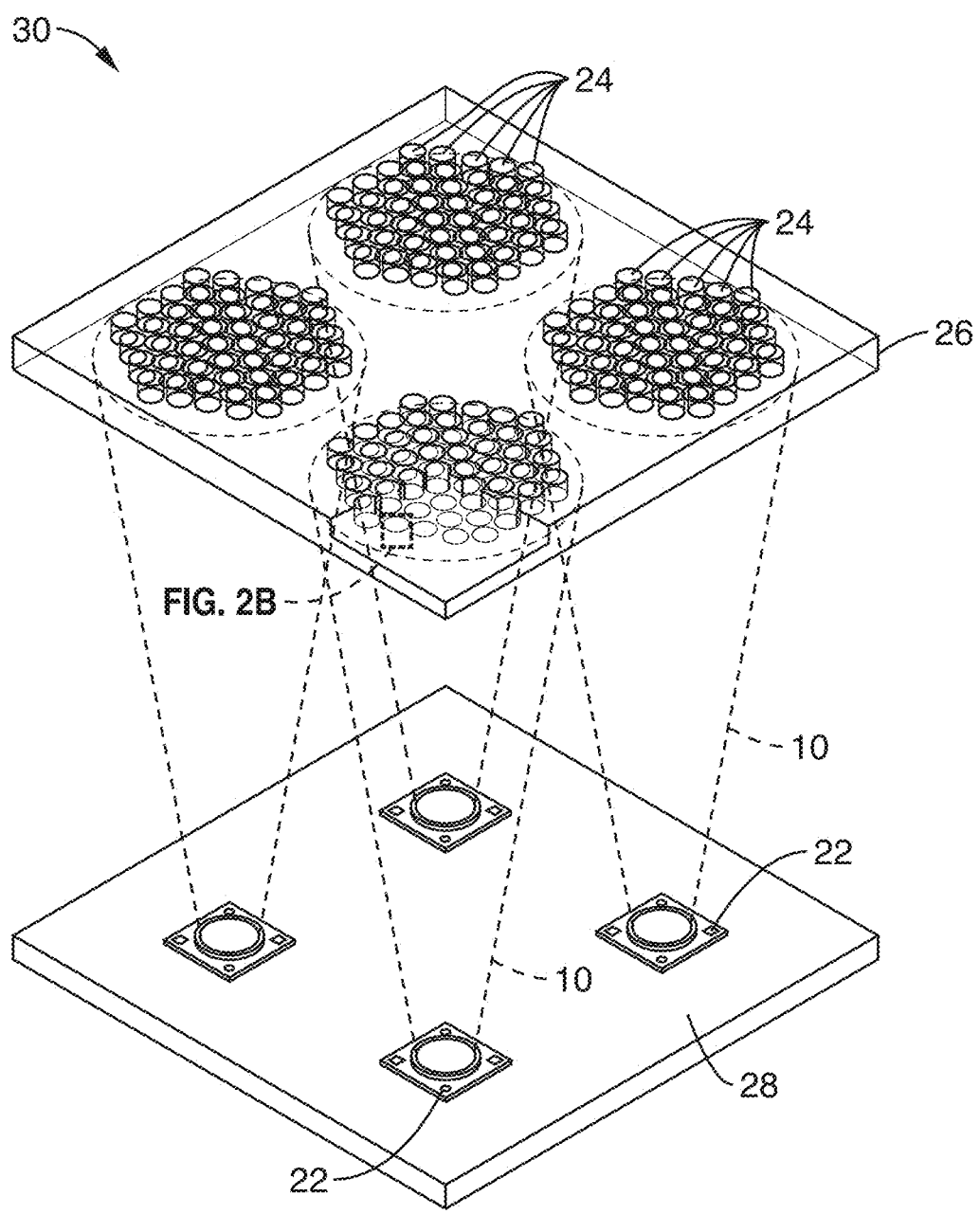
FIG. 2A and FIG. 2B show a schematic diagram of a system for ultrafast photonic PCR using thin gold (Au) film as a light-to-heat converter and excitation light from the light-emitting diodes
Figure 2B:
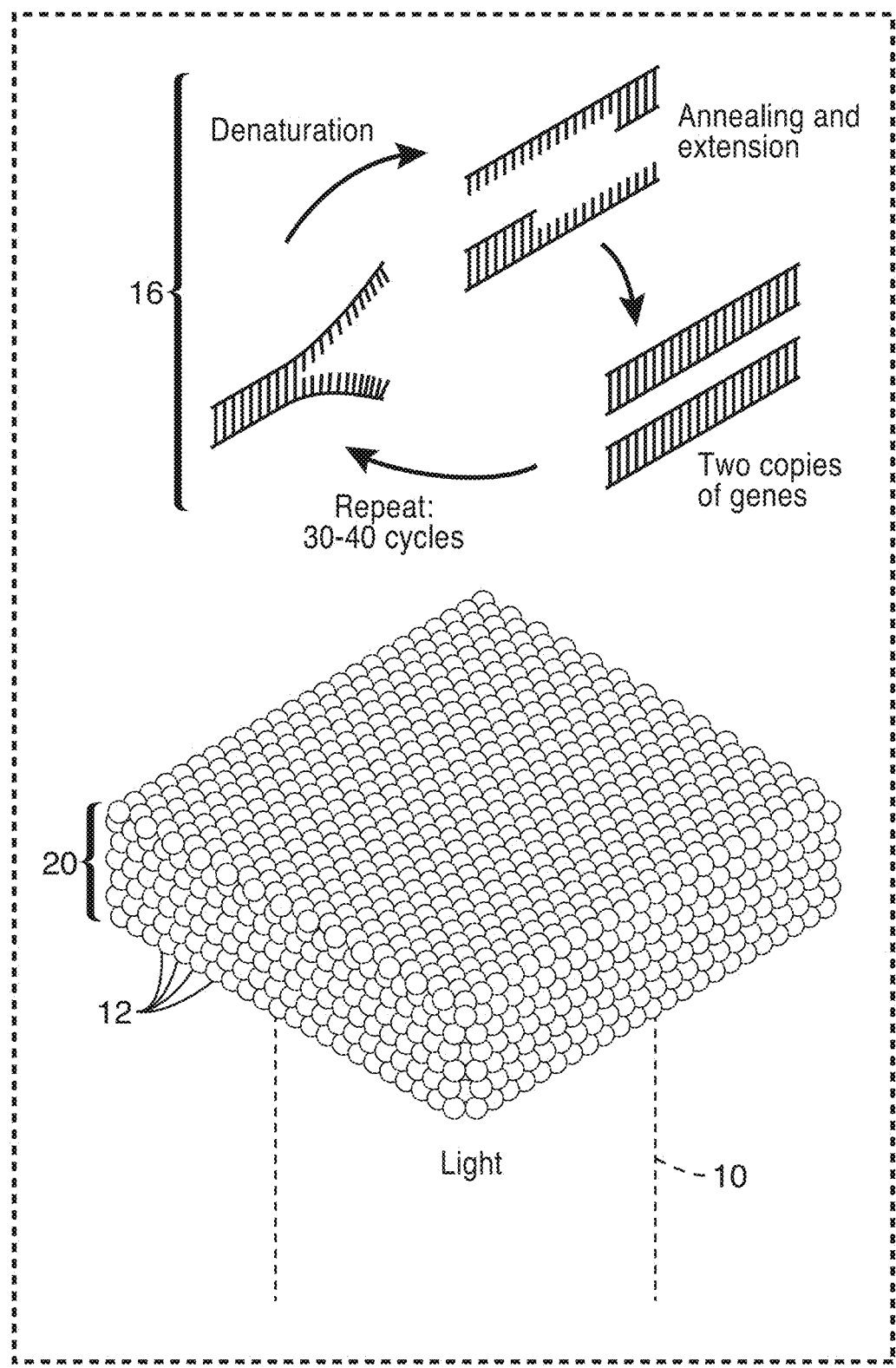
Figure 3:
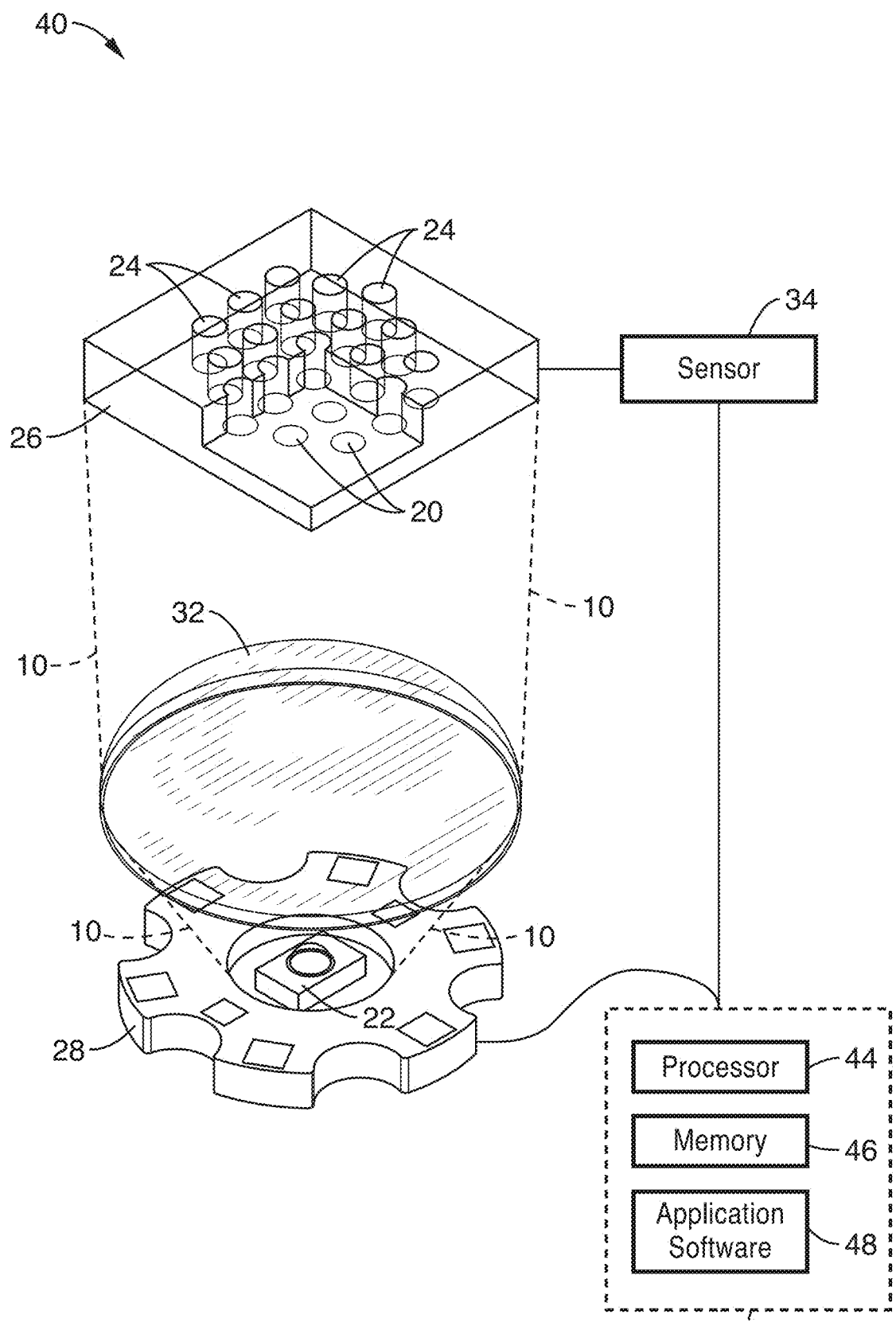
FIG. 3 shows a schematic diagram of a LED-driven ultrafast photonic PCR system.

Referring to FIG. 1 through FIG. 3, a novel ultrafast photonic PCR system and method are shown, combining the use of thin Au film as a light-to-heat converter and a light source such as light-emitting diodes (LEDs) as a heat source.

FIG. 1 shows a schematic diagram of the plasmonic photothermal light-to-heat conversion and subsequent heating of surrounding medium through the ultrafast photon-electron-phonon couplings in accordance with the technology of the present description. Light (photon) 10 is directed toward the Au molecule 12 to generate photon coupling 14 and resultant heat generation of the medium 16 (PCR mixture).

In considering photon interaction with materials, the absorption of photons is often treated as heat. When the photons 10 from the excitation source reaches the surface of thin Au molecule 12, plasmon-assisted strong light absorption can occur. This in turn excites electrons near the surface to higher energy states, generating hot electrons within 100 fs. These hot electrons can reach a temperature of several thousand degrees Kelvin due to their small electronic heat capacity. They are also capable of rapidly diffusing throughout the thin Au film, creating a uniform distribution of hot electrons. Rapid heating is followed by cooling to equilibrium by energy exchange between the hot electrons and the lattice phonons after 5~10 ps. Thus, overall, when the Au is illuminated, a large temperature difference between the hot metal surface and the cooler surrounding solution 16 occurs, resulting in the heating 14 of the surrounding solution 16 in a long time scale over 100 ps.

FIG. 2A and FIG. 2B (exploded view) show a schematic diagram of a system 30 for ultrafast photonic PCR using thin plasmonic (e.g. gold (Au)) film 20 as a light-to-heat converter and excitation light 10 from a light source 22 (e.g., LEDs). In one embodiment, the thin films 20 are fabricated with nanometer sized grain prepared by electron beam evaporation, and are configured to enhance light absorption through surface plasmon resonance, leading to fast plasmonic heating of thin Au film.

While the plasmonic thin film 20 is detailed throughout the description as being Au, it is appreciated that such selection of materials is for exemplary purposes only, and any number of plasmonic materials may be selected for plasmonic heating of the sample solution 16. For example, the plasmonic thin film 20 may comprise gold (Au), silver (Ag), palladium (Pd), platinum (Pt), nickel (Ni), titanium (Ti), chromium (Cr), germanium (Ge), tungsten (W), iridium (Ir), etc., or any combination or alloy thereof. The plasmonic thin film can be multi-layer metallic structure composed of the gold (Au), silver (Ag), palladium (Pd), platinum (Pt), nickel (Ni), titanium (Ti), chromium (Cr), germanium (Ge), tungsten (W), iridium (Ir), etc., or any combination or alloy thereof. Furthermore, the plasmonic thin film can be graphene, graphene oxide, graphite, or carbon nanotubes (CNTs), or plasmonic thin film can be graphene, graphene oxide, graphite, or carbon nanotubes (CNTs), or a hybrid or materials composed thereof.

Furthermore, while the light source 22 is detailed throughout the description as being one or more LED's, it is appreciated that such selection is made for exemplary purposes only, and any number of different light sources may be selected for illumination of the plasmonic thin film 20. For example, the light source 22 may comprise LEDs, diode lasers, a diode laser array, a quantum well (vertical)-cavity laser, or combination or array thereof. Additionally, the emission wavelength of light source may be an ultraviolet (UV), visible, or infrared (IR), etc.

As seen in the exploded detail of FIG. 2B, the PCR mixture 16 is subjected to a three-state thermal cycling, comprising of 2 or 3 discrete temperatures for denaturation (phase 1), and annealing and extension (phase 2), with resulting in the nucleic acid amplification phase (phase 3) through the polymerase chain reaction (PCR). As further illustrated in FIG. 2, an array of LED's 22 may be disposed on substrate 28 for illuminating arrays of PCR wells 24 that are disposed in transparent or translucent platform 26. For a multiple PCR reaction as depicted in FIG. 2, each LED 22 may be modulated separately to have unique annealing temperatures for each primer design.

The thin Au film 20 deposited within wells 24 is used as a light-to-heat converter, serving as a source of plasmonic (i.e. plasmon-excitable) photothermal heating for the PCR thermal cycling as shown in FIG. 2.

Besides driving multiple PCR reactions with single LEDs, multiple well plates integrated with LED arrays may be used for multiplexed PCR by modulating each LED 22 to have unique annealing temperatures for the various primer designs. Such multiple well LED array PCR thermal cycler configuration is ideal for multiplexed ultrafast PCR at POC diagnostics, because it could perform multiple tests at once.

FIG. 3 shows a schematic diagram of a LED-driven ultrafast photonic PCR system 40. Continuous-wave light from blue LEDs 22 is focused on a plasmonic Au thin-film 20 (deposited on bottom of PCR wells 24) through the focus lens 32. Lens 32 may include a configured to produce an evenly distributed light exposure of the plasmonic thin film 20 to light from the light source the peak wavelength of the LEDs was 450 nm. (Blue LED I). The Au-coated PCR wells 24 were formed in a polymeric (e.g. poly (methyl methacrylate) (PMMA) platform 26.

Platform 26 preferably comprises a transparent or translucent composition to allow light to pass through to the thin film 20. While the platform 26 is detailed throughout the description as generally comprising PMMA, it is appreciated that such selection of materials is for exemplary purposes only, and any number of polymeric or translucent/transparent materials may be selected for use as the platform. The support platform 26 may also comprise 2D or 3D microstructures or nanostructures that may comprise one or more of a pillar array, 1D or 2D grating, photonic crystal, hemi-sphere, or other patterned or random structures. In one embodiment, the platform comprises nanoplasmonic structures or nanoplasmonic feedback laser cavity on the surface of the wells the are configured to be illuminated at a resonance wavelength of nanoplasmonic structures and duration that causes plasmonic photothermal heating of the nanoplasmonic structures A temperature sensor 34 is coupled or directed at the platform 26 for measuring the temperature of the sample 16 and/or thin film 20. Such temperature sensor 34 may comprise a number of possible sensor types, such as thermocouple or camera (e.g. IR camera) directed at the platform 26.

It is also appreciated that PCR system 40 may be integrated or compatible with a diagnostic device, such as digital camera, photodiode, spectrophotometer or the like imaging device (not shown, but may be in place of or integrated with of IR camera 52 shown in FIG. 11) for the real-time detection of nucleic acids and/or the fluorescence signal of the sample solution 16. In some configurations the camera may be smart phone camera, wherein the smart phone comprises application software for analysis of the sample solution 16.

In a preferred embodiment, the sensor and LED's 22 may be coupled to a computing unit 42 for acquisition of sensor data and control of the LED's 22. Computing unit 42 generally comprises a processor 44, and memory 46 for storing application software 48 executable on the processor 44 for driving the LED 22 (e.g. controlling LED timing, intensity/injection current, etc.), acquiring data from sensor 34 and/or processing data from a diagnostic device such as a digital camera real-time detection of nucleic acids and/or the fluorescence signal of the sample solution 16. Computing unit 42 may comprise a separate computer or device, or may be integrated into a microcontroller module with the remainder of the components. Acquired data and/or a user interface may be output on a display (not shown) integrated with or coupled to the computing unit 42.

In one embodiment, strong light absorption of the thin Au film 22 (e.g. 65%, 120 nm thick) generates heat due to the plasmonic photothermal light-to-heat conversion by photon-electron-phonon coupling at the thin Au film 20, followed by heating of surrounding solution 16 with a maximum temperature of over 150° C. within 3 min. Ultrafast 30 thermal cycles (heating rate of $12.79 \pm 0.93°$ C. $\sec^{-1}$ and cooling rate of $6.6 \pm 0.29°$ C. $\sec^{-1}$) from 55° C. (point of annealing) to 95° C. (point of denaturation) are accomplished within 5 min for successful amplification of λ-DNA.

The PCR systems shown in FIG. 1 through FIG. 3 are ideal for POC diagnostics, due to ultrafast thermal cycling capability, multiplexed PCR, low power consumption for the PCR thermal cycling (in current set-up, up to ~3.5 W), low cost and simple configuration for system level integration. Furthermore, the photonic-based heating procedure of the present description may be generally integrated into a variety of devices or procedures, including on-chip thermal lysis and heating for isothermal amplifications.

Example 1 a. Fabrication

Several 4 mm-thick poly(methyl methacrylate) (PMMA) sheets 26 were cut with a VersaLASER VL-200 laser cutting system (Universal Laser System, Inc.) to make reaction wells 24 with a 4 mm diameter. A 1.5 mm-thick bottom PMMA sheet were attached to the top sheet containing reaction wells were bonded together using the thermal bonding. Thermal bonding was performed at 84° C. with pressure of 1.0 metric ton after UV/Ozone treatment of PMMA sheet for 10 min. The thin Au films 20 of different thicknesses were deposited by electron beam evaporation under base pressure of $2 \times 10^{-7}$ Torr. The thin Au film 20 was then passivated with thin poly(dimethylsiloxane) (PDMS) by dropping 3 μL of PDMS into the well and curing in the oven for 2 hrs to prevent PCR reaction inhibition by the thin Au film and thermocouple.

b. Simulation

COMSOL Multiphysics software (Ver. 4.3) was used for performing simulations. The detailed geometry and materials properties for simulation are shown in FIG. 7 and Table 1. A thin Au film was placed on a PMMA substrate and water was disposed on the top of Au film. Different thicknesses (10 nm, 20 nm, 40 nm, 80 nm, and 120 nm) of thin Au film were applied to the simulation to calculate the absorption of the Au films and subsequent resistive heat generation. The plane wave with x-polarized electric field travels in the positive z direction in the coordinate shown in FIG. 7. The permittivities of PMMA and water were 3 and 1.77, respectively.

A set of electromagnetic simulations was performed to theoretically characterize the plasmonic photothermal light-to-heat conversion of the Au films. The electromagnetic (EM) field and resistive heat distributions were calculated for 10 nm and 120 nm thick Au films on a PMMA substrate. FIG. 4A and FIG. 4B show images for electromagnetic field on 10 nm and 120 nm thick Au films on PMMA substrate, respectively. FIG. 4C and FIG. 4D show images for resistive heat distributions on 10 nm and 120 nm thick Au films on PMMA substrate, respectively. FIG. 4E shows a plot of calculated absorption spectra of the thin Au films with different thickness. FIG. 4F shows a plot of light-to-heat conversion efficiency of the thin Au films averaged over emission wavelength from 3 different LEDs as a function of Au films thickness.

As expected from skin depth, $$\delta = \sqrt{\frac{2}{\omega \mu \sigma}}$$

where ω: angular frequency, μ: permeability, σ: conductivity, the thickness of thin Au film determines the amount of light to heat conversion. Upon a normal incidence of a 450 nm wavelength light source, the 10 nm thick Au film transmits an enormous amount of EM energy (FIG. 4A), and the heat conversion energy is saturated along the film depth (FIG. 4C). However, the 120 nm thick Au film absorbs most of the incident light (FIG. 4B) and subsequently generates more heat in the Au film by converting light into heat (FIG. 4D).

FIG. 4E shows a plot of calculated absorption spectra of the thin Au films with different thickness, Light-to-heat conversion efficiency of the thin Au films averaged over emission wavelength from 3 different LEDs as a function of Au films thickness. The blue LED with 450 nm peak wavelength shows the highest averaged light-to-heat conversion efficiency, illustrating that an increase in thickness of thin Au film, in the range of 10 to 120 nm, corresponds to an increase in optical absorption. Significant increase of optical absorption below 540 nm wavelength could be attributed to the plasmonic electron resonance of gold. As a result, the averaged light-to-heat conversion efficiency over emission wavelength from each LED increases with increased Au film thickness for the 3 different LEDs (Blue I at 450 nm, Blue II at 480 nm, and Green at 530 nm). as shown in FIG. 4F (see also FIG. 8). It is noteworthy that the blue LEDs with a peak emission wavelength of 450 nm shows highest light-to-heat conversion efficiency with thin Au film.

c. Test Setup

A test setup similar to the system 40 shown in FIG. 3 was used for experimentation. LEDs 22 (Luxeon Rebel royal blue star LEDs with a peak wavelength of 447.5 nm, 890 mW at 700 mA injection current) were used for plasmonic photothermal heating of the thin Au film 20 with a Keithley 2400 source meter (not shown). To focus the light from the LEDs, a Carclo 20 mm fiber coupling optic 32 was employed. The temperature of the solution was monitored and recorded in real time by a type-K insulated thermocouple (OMEGA Engineering) for thermal cycling. Temperature cycling using an LED, 80 mm cooling fan (not shown), source meter and thermocouple was controlled through LabVIEW as the application software. A National Instruments (NI) 16 channel thermocouple module (not shown) with high speed mode, auto zero and cold junction compensation (CJC) was used for accurate temperature acquisition from the type-K thermocouple.

d. Preparation of the PCR Reagent and DNA Template

A template λ-DNA and Takara Z-Taq DNA polymerase (2.5 U/μL), 10× Z-Taq Buffer ($Mg^{2+}$ plus, 30 mM) and dNTP Mixture (2.5 mM each) were used. Forward primer and reverse primer were purchased from Integrated DNA Technologies. The reactions used to amplify a 98 base pair (bp) λ-DNA target with Z-Taq DNA polymerase included 0.5 μL Z-Taq DNA polymerase, 5 μL of 10× Z-Taq Buffer, 4 μL of dNTP mixture, 4.5 μL of 10 μM primers (each), 10 μL of bovine serum albumin (BSA) (50 μg), and was brought to 50 μL with PCR grade water. The final concentration of template λ-DNA was 0.1 ng/μL. The 10 μL of PCR mixture was placed within an Au-coated PMMA PCR wells for photonic PCR, and then covered with 30 μL of mineral oil to prevent evaporation during thermal cycling. After amplification, the mixture of 10 μL of PCR product and 10 μL of E-Gel sample loading buffer (Invitrogen) was loaded onto E-Gel 2% agarose gels with SYBR Safe (Invitrogen), and ran in an E-Gel base (Invitrogen) for 30 min. A 1 Kb DNA ladder was used to confirm the size of product.

e. LED-Driven Photonic PCR Thermal Cycler

Figure 5A:
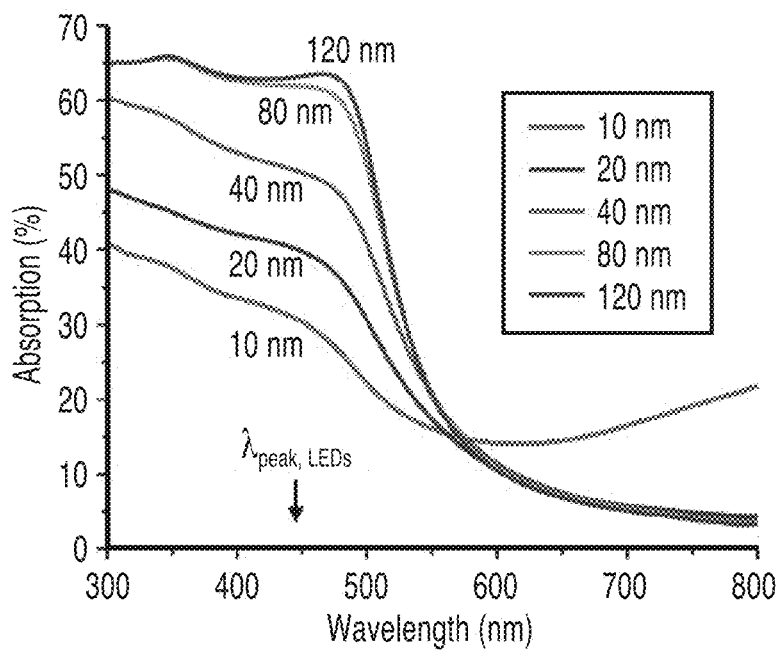
Figure 5B:
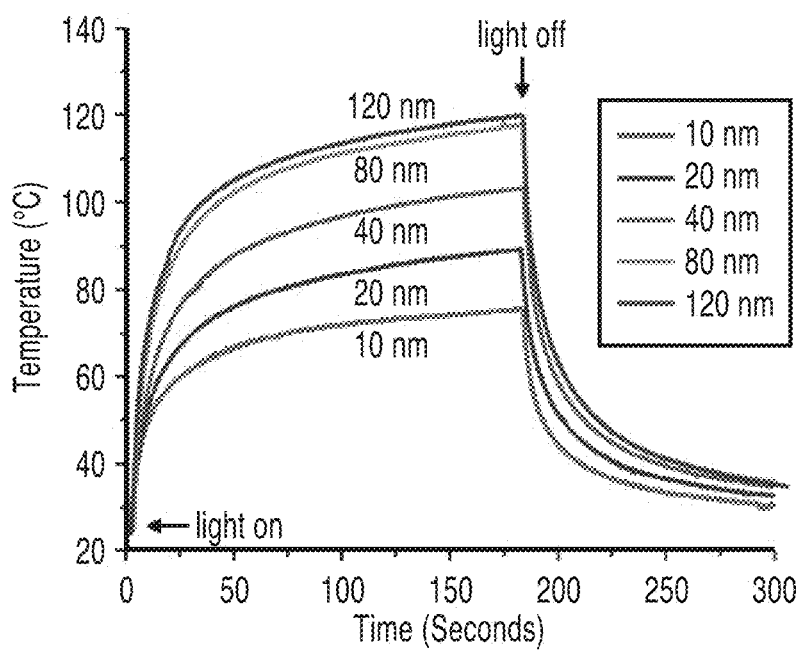
Figure 5C:
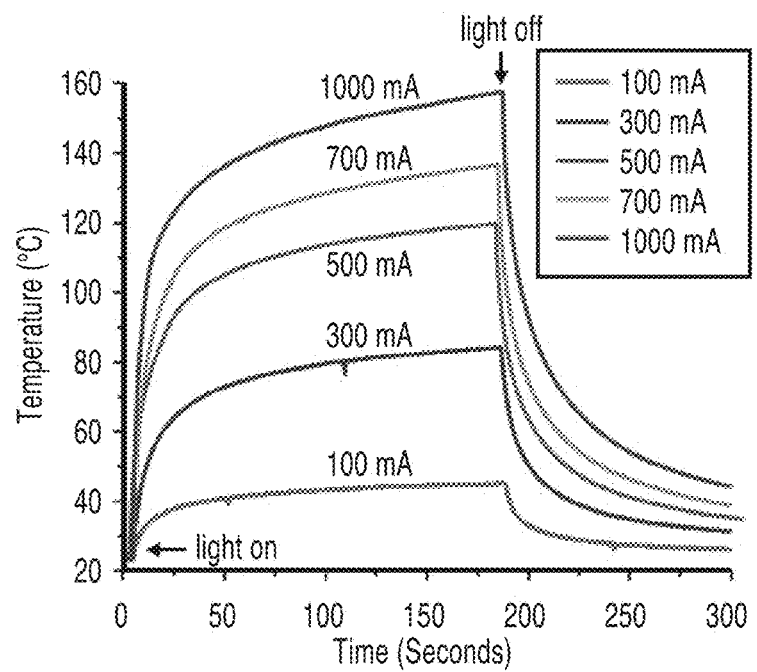
Figure 5D:
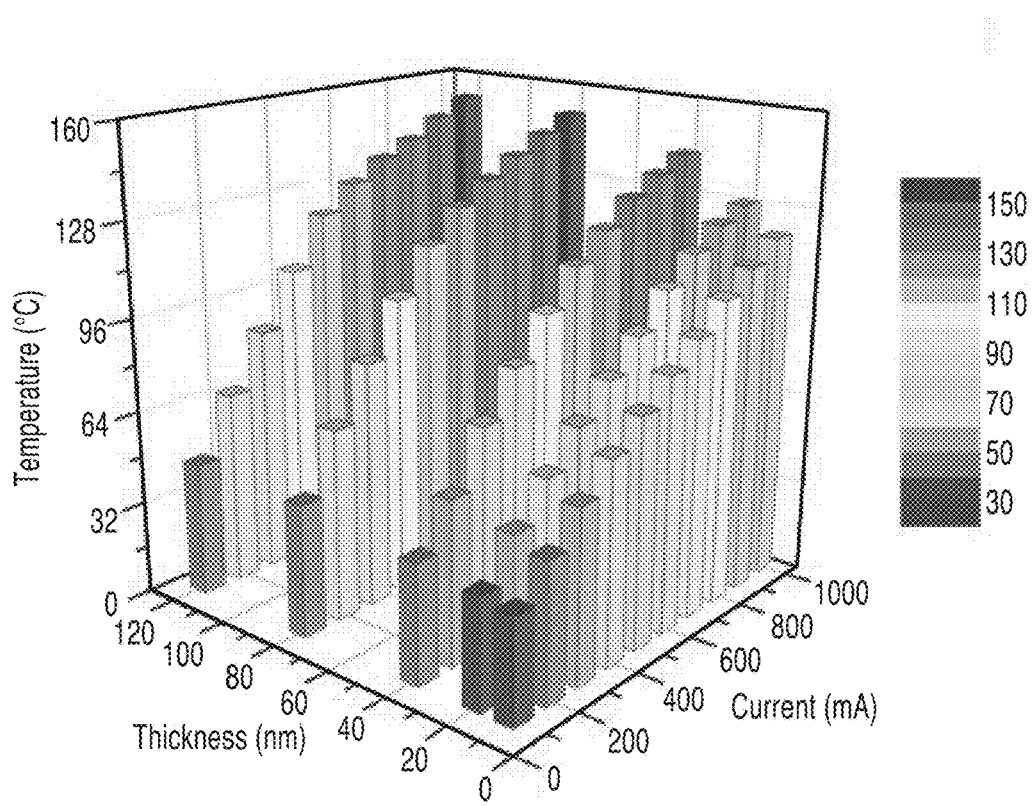
Figure 5E:
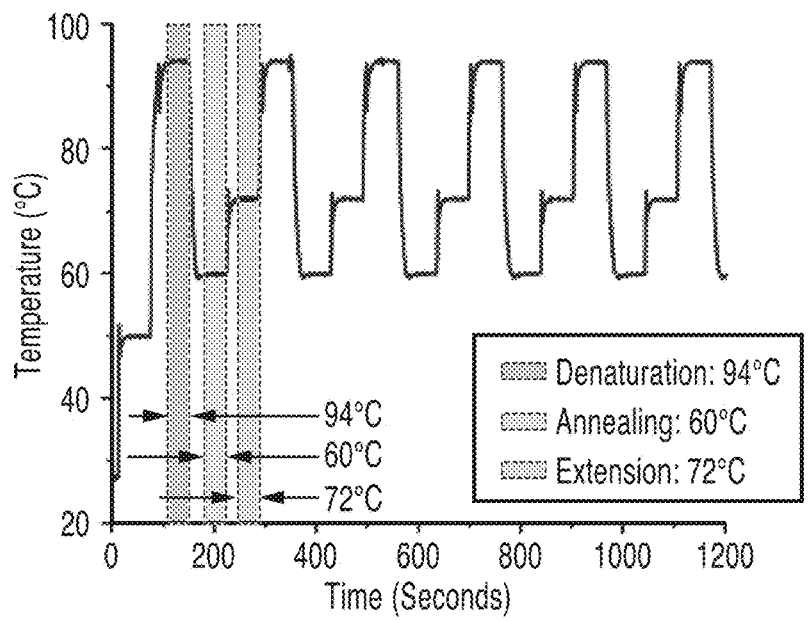
Figure 5F:
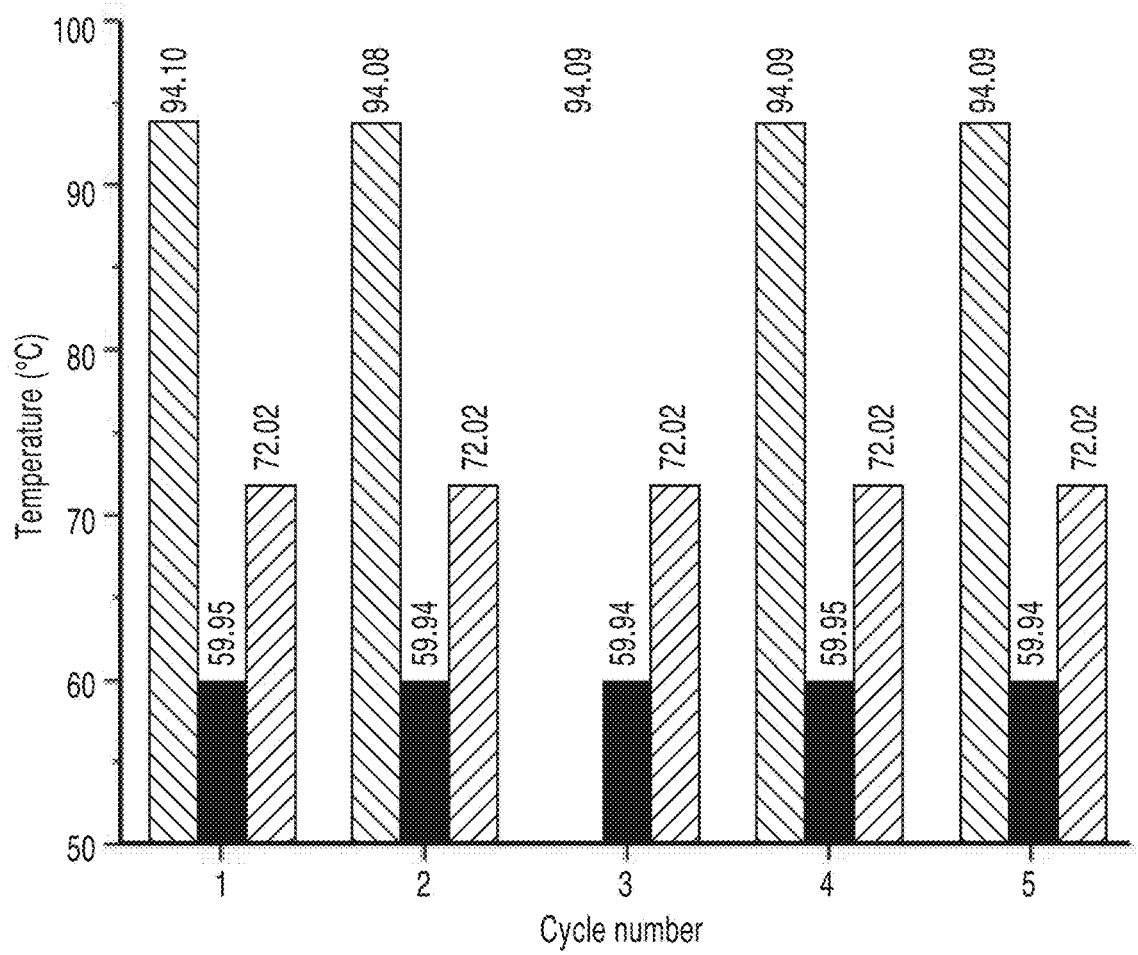

FIG. 5A through FIG. 5F show plots of LED driven photothermal heating of the thin Au film and PCR thermal cycling. FIG. 5A shows absorption spectra of the thin Au films with different thickness. Absorption (%)=100−Transmittance (%)−Reflectance (%). FIG. 5B shows temperature profiles of liquids as a function of Au film thickness at a 500 mA injection current. FIG. 5C shows temperature profiles of liquids as a function of injection current of LEDs with 120 nm-thick Au film. The blue LED with 450 nm peak wavelength was used. FIG. 5D shows a 2D map showing the distribution of liquid temperature with different thickness of the thin Au film and injection current of LEDs after heating for 3 min. FIG. 5E illustrates LED driven photonic PCR thermal cycling of 3 different temperatures: 94° C. (denaturation), 60° C. (annealing) and 72° C. (extension). FIG. 5F shows temperature control and low temperature variations for PCR thermal cycling. Average values with standard deviation at 94° C., 60° C. and 72° C. were 94.09±0.17° C., 59.94±0.13° C. and 72.02±0.12° C., respectively.

Referring to FIG. 5A, the optical absorption spectra of thin Au films with different thicknesses deposited on PMMA substrate are shown. The simulation results can help determine when the strongest light absorption occurs, as this is critical to maximizing photothermal heating. As the thickness of thin Au film increases, the optical absorption also increases, showing 65% absorption at the peak wavelength (450 nm) of excitation LEDs in the 120 nm-thick Au film.

With the photonic PCR thermal cycler 40 shown in FIG. 3, the light from the LEDs 22 is continuous-wave and randomly polarized. Therefore, the efficiency of light-to-heat conversion would be lower in this case than a pulsed laser, because as electrons are excited to higher energy states, the probability of further excitation decreases. Despite the possibility of lower light-to-heat conversion efficiency than a pulsed light source, however, LEDs require minimal power consumption and are extremely low in cost compared to laser sources, making LEDs an ideal PCR heating source for POC testing. The component cost of the instruments for our ultrafast photonic PCR thermal cycle can be fabricated for less than US $100, including the LEDs, focus lens and driver, with the Labview (as part of application software 48) and data acquisition board for temperature control integrated into a microcontroller module (e.g. computing module 42 in FIG. 3).

The maximum power consumption of an LED is generally around 3.5 W at 1 A injection current. FIG. 5B shows the temperature profiles of a 10 µL volume of solution (here, glycerol was used to show maximum heating temperature) with different thickness thin Au films at a fixed injection current of 500 mA. The maximum temperatures are increased as the thickness of thin Au film increases from 10 nm to 120 nm due to the increasing optical absorption.

The photothermal heating of the 120 nm-thick Au film was further characterized as a function of injection current as shown in FIG. 5C, because the heating rate is determined by the amount of dissipated power (i.e., an injection current of LEDs). FIG. 5D summarizes the temperature of a solution after 3 min heating with different thickness Au films and varying injection current (see Table 2). These results clearly indicate that the maximum temperatures are increased with an increase of Au film thickness to 120 nm and an increase of injection current to 1 A.

Complete PCR thermal cycling, consisting of 3 representative temperatures (94° C. for denaturation, 60° C. for annealing, and 72° C. for extension), is demonstrated using an LED-driven photonic PCR thermal cycler, as shown in FIG. 5E. To prevent evaporation during thermal cycling, 10 µL of PCR buffer was covered with 30 µL of mineral oil. The averages and standard deviations at each temperature were obtained from the temperature profile and the results are 94.09±0.17° C. at 94° C., 59.94±0.13° C. at 60° C. and 72.02±0.12° C. at 72° C., respectively, showing excellent temperature accuracy and stability. The initial temperature fluctuation before reaching setting temperature may be further reduced by optimizing the proportional-integral-derivative (PID) controller value in Labview.

f. Ultrafast Thermal Cycling and Nucleic Acid Amplification

In order to determine maximum heating and cooling rates, a thermal cycle was performed, whereby the solution (here, 5 µL of PCR mixture covered with 30 µL of mineral oil) temperature was rapidly cycled between 55° C. and 95° C. The temperature range mirrors the same denaturation (95° C.) and annealing (55° C.) temperatures.

FIG. 6A through FIG. 6C show plots and images of ultrafast thermal cycling and DNA amplification. FIG. 6A is a plot of representative temperature profiles of 30 ultrafast photonic PCR thermal cycles from 95° C. (denaturation) to 55° C. (annealing and extension). The 5 µL of PCR buffer was covered with 20 µL of mineral oil to prevent evaporation during thermal cycling. FIG. 6B shows plot of heating and cooling rates obtained from the ultrafast photonic thermal cycling. FIG. 6C is an image showing formation of product from the photonic PCR thermal cycler in comparison with a bench-top thermal cycler using a λ DNA template. Heating and cooling rate were 12.79±0.93° C. sec$^{-1}$ and 6.6±0.29° C. sec$^{-1}$, respectively.

Referring to FIG. 6A, the ultrafast photonic 30 cycles within 5 minutes are shown. Using the thermal cycling result, heating and cooling rates were calculated by measuring the temperature difference between successive temperature maxima and minima, then dividing by the time interval between them. The average rates and sample standard deviations were obtained as shown in FIG. 6B. The average heating and cooling rates obtained are 12.79±0.93° C. sec$^{-1}$ and 6.6±0.29° C. sec$^{-1}$, respectively. The amplification of λ-DNA was performed to verify our photonic PCR method.

After running PCR reactions as shown in FIG. 6C, the amplicons were visualized by E-Ge 2% agarose gels with SYBR Safe. Lane 1 represents the 1 kb DNA marker, lane 2 and 3 are the PCR product from ultrafast photonic PCR with different cycle numbers (94° C. for 0 sec, 62° C. for 0 sec), lane 4 and 5 contain positive controls produced from a standard thermal cycle condition (94° C. for 1 sec, 62° C. for 1 sec, 60 cycles) by a bench-top thermocycler (Bio-Rad C1000 Thermal Cycler). A single major band (98 bp) was detected near 100 bp in photonic PCR (Lane 2 and 3). This indicates that the λ-DNA was successfully amplified using the ultrafast photonic PCR method and system of the present description. The weak band intensity from the PCR product amplified by photonic PCR could be attributed to the lower amplification efficiency compared to a traditional bench-top thermal cycler. Currently, only thin Au film acts as a 2-dimensional photothermal heater, leading to a temperature gradient of the solution, leading to potentially lower amplification efficiency of PCR. This limitation can be improved by utilizing a 3-dimensional substrate in the PCR chamber for uniform photothermal heating of PCR mixture. Amplification time as well as reagent consumption could be further reduced, simultaneously improving the efficiency of the PCR reaction by faster molecular diffusion and uniform solution temperature.

FIG. 8 shows normalized light emission spectra measured from 3 different LEDs with peak wavelengths of 450 nm (Blue I), 480 nm (Blue II) and 530 nm (Green), respectively. Blue I was generated with Luxeon Rebel royal blue star LEDs with a peak wavelength of 447.5 nm, 890 mW at 700 mA injection current. Blue II was generated with Luxeon Rebel blue star LEDs with a peak wavelength of 470 nm, 70 lm at 700 mA injection current. Green was generated with Luxeon Rebel green star LEDs with a peak wavelength of 530 nm, 161 lm at 700 mA injection current. The spectra were measured using Ocean Optics USB 2000+ spectrophotometer.

FIG. 9A and FIG. 9B show transmittance and reflectance spectra, respectively, of the thin Au films on PMMA substrate with different thickness. Transmittance and reflectance spectra were measured using a Shimadzu UV-3101PC UV-Vis-NIR spectrophotometer. An integrating sphere was employed to measure diffuse reflection as well as specular reflection.

FIG. 10 is a plot showing a comparison of 31 ultrafast thermal cycles from 62° C. to 94° C. with and without cooling fan to show the effect of cooling fan to further reduce the power consumption of photonic PCR thermal cycler.

Example 2

FIG. 11 shows the schematics of experimental set up 50 for LED driven plasmonic heating of thin Au films. Blue LEDs 22 with 447.5 nm peak wavelength were used for light illumination and the light from LEDs was focused by commercially available plastic lens 32. The thin Au films 20 with nanometer sized grain were deposited by an electron beam evaporation method. The surface temperature of liquid 16 was measured by long wavelength infrared (LWIR) camera 52.

FIG. 12 shows the demonstration of fast thermal cycle using 2 µL of glycerol from 50° C. to 90° C. for 9 min using LED driven plasmonic heating of thin Au films. The injection current was 1 A, and the thickness of thin Au film was 56 nm.

FIG. 13A shows the temperature changes of liquid with different thin Au films thickness. As the thickness of Au film increase, the maximum temperature of liquid is increased, as shown in FIG. 13B. The temperature of liquid was rapidly decreased after turn off of LEDs.

FIG. 13C shows the absorbance spectra of thin Au films with different thickness. The absorption peak around 440 nm is well matched with peak wavelength of LEDs. As the thickness of Au film increase, the absorbance is also increased, resulting in the increase of maximum temperature. FIG. 13D and FIG. 13E show images of the Au film 20 at 56 nm and 96 nm, respectively.

FIG. 14A shows the temperature changes of liquid with different injection current. The thickness of Au film is 64 nm. As the injection current increase, the maximum temperature is increased as shown in FIG. 14B. Therefore, the temperature can readily be controlled by simply changing the injection current of LEDs. The maximum ramp rate is calculated at each injection current and it reaches up to 7° C./sec with a 1 A injection current.

FIG. 15 shows the temperature stability of LED driven plasmonic heating of thin Au films. The 50° C. and 90° C. are representative annealing and denaturation temperatures, respectively, for a fast 2-step PCR setup. The temperature changes at 50° C. and 90° C. are ±0.5 and ±0.7° C., showing good temperature stability.

FIG. 16 and FIG. 17 illustrate an exemplary PCR using LED driven plasmonic heating of thin Au films. The thickness of Au film is 64 nm. The detailed PCR condition is described in figure. FIG. 16 shows temperature profiles of thermal cycling measured by IR camera during PCR reaction. The temperature profile measured by IR camera is a little different, because the IR camera measures only the surface temperature of liquid. FIG. 17 shows that the LED driven plasmonic thermal cycler through this invention shows comparable nucleic acids amplification product to conventional bench top thermal cycler.

In summary, a novel ultrafast photonic PCR system is disclosed that utilizes plasmonic photothermal heating of thin Au films driven by LEDs. A thin Au film-based light-to-heat converter was designed and fabricated to heat a PCR solution over 150° C. by harnessing gold plasmon-assisted high optical absorption. Ultrafast thermal cycling from 55° C. (annealing) to 95° C. (denaturation) was achieved within 5 minutes for 30 cycles with ultrafast heating (12.79±0.93° C. sec$^{-1}$) and cooling (6.6±0.29° C. sec$^{-1}$) rates. Nucleic acid (λ-DNA) amplification using our ultrafast photonic PCR thermal cycler was successfully demonstrated. The systems and methods of the present description are shown to provide a simple, robust and low cost photonic PCR technique, with ultrafast thermal cycling capability, which is ideal for POC molecular diagnostics, having the following beneficial attributes: 1) affordability (less expensive system with a LED and lens); 2) portability (compact and light PCR system without a heating block); 3) simplicity (use of use with disposable PCR chip); 4) user-friendly interface with LED driver and display; 5) rapid and robust PCR without environmental stress; 6) generally equipment free—only LED and microcontroller modules may be required and incorporated with use of cell-phone camera; and 7) durability in harsh environments & low power consumption. While the tested set-up was based on only one PCR well, integration of multiple wells and an array of LED's is contemplated to allow for high-throughput and multiplexed amplification, as well as optimizing the PCR reaction chamber for uniform heating.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An apparatus for nucleic acids amplification, comprising: a support platform comprising one or more wells configured to hold a sample; a plasmonic thin film disposed within the one or more wells; and a light source; wherein the light source is configured to be directed at the platform such that exposed light from the light source to generates plasmonic photothermal light-to-heat conversion within the plasmonic thin film and subsequent heating of the sample.

2. The apparatus of any preceding embodiment, further comprising: a lens disposed between the light source and the support platform; wherein the lens is configured to focus the exposed light at the one or more wells.

3. The apparatus of any preceding embodiment, further comprising a temperature sensor configured to monitor the temperature of the sample.

4. The apparatus of any preceding embodiment, further comprising: a controller coupled to one or more of the light source and temperature sensor; the controller configured for controlling one or more of data acquisition from the temperature sensor and actuation of the light source.

5. The apparatus of any preceding embodiment, wherein the controller is configured for controlling actuation of the light source to modify one or more of exposure duration and injection current at the plasmonic thin film.

6. The apparatus of any preceding embodiment, wherein the plasmonic thin-film sheet comprises a nanometer sized grain to enhance light absorption through surface plasmon resonance.

7. The apparatus of any preceding embodiment, wherein the platform comprises a translucent or transparent polymer.

8. The apparatus of any preceding embodiment, wherein the temperature sensor comprises a long wavelength infrared (LWIR) camera oriented adjacent to the sample.

9. The apparatus of any preceding embodiment, further comprising a diffuser associated with the focusing lens to evenly distribute the exposed light to the plasmonic thin film.

10. The apparatus of any preceding embodiment, wherein the light source comprises one or more LED's having a wavelength selected for maximum light absorption within the plasmonic thin film.

11. The apparatus of any preceding embodiment, further comprising: a digital camera, photodiode or spectrophotometer for the real-time detection of nucleic acids within the sample.

12. The apparatus of any preceding embodiment, wherein the platform comprises 2D or 3D microstructures or nanostructures in the form of one or more of a pillar array, 1D or 2D grating, photonic crystal, hemi-sphere.

13. A method for nucleic acids amplification, comprising: disposing a fluid sample within the one or more wells having a plasmonic thin film; directing a light source at the plasmonic thin film to generate plasmonic photothermal light-to-heat conversion within the plasmonic thin film; and heating the sample as a result of the light-to-heat conversion within the plasmonic thin film.

14. The method of any preceding embodiment, further comprising: focusing light from the light source at the one or more wells.

15. The method of any preceding embodiment, further comprising: monitoring the temperature of the sample.

16. The method of any preceding embodiment, further comprising: controlling one or more of data acquisition from a temperature sensor and actuation of the light source.

17. The method of any preceding embodiment, wherein controlling actuation of the light source comprises controlling one or more of exposure duration and injection current at the plasmonic thin film.

18. The method of any preceding embodiment, wherein the plasmonic thin-film sheet comprises an Au film with a nanometer sized grain to enhance light absorption through surface plasmon resonance.

19. The method of any preceding embodiment: wherein the one or more wells are formed in a translucent or transparent platform; wherein the light from the light source is directed through at least a portion of the platform to the plasmonic thin film.

20. The method of any preceding embodiment, further comprising: diffusing the focused light to evenly distribute the light to the plasmonic thin film.

21. The method of any preceding embodiment, wherein the light is emitted at a wavelength selected for maximum light absorption within the plasmonic thin film.

22. The method of any preceding embodiment, further comprising: detecting a fluorescence signal within the sample.

23. A plasmonic heater apparatus for nucleic acids amplification, comprising: a substrate having a plurality of reaction wells configured for holding a sample; wherein a surface of each of the plurality of reaction wells is covered with a plasmonic thin film; and a light source directed at the substrate; the light source configured to illuminate the plasmonic thin film at a wavelength and duration that causes photothermal heating of the plasmonic thin film and subsequent heating of the sample.

24. The apparatus of any preceding embodiment, further comprising: at least one temperature sensor configured to monitor the temperature of the sample in each well.

25. The apparatus of any preceding embodiment, further comprising: (a) a control module coupled to the temperature sensor and the light source; (b) the control module comprising a processor and a memory storing instructions executable on the processor; (c) said instructions, when executed by the processor, performing steps comprising: (i) monitoring sample temperature; and (ii) actuating the light source at a frequency and duration to produce selected sample temperatures over time.

26. The apparatus of any preceding embodiment, wherein said instructions when executed by the processor further perform steps comprising detecting or a fluorescence signal within the sample.

27. The apparatus of any preceding embodiment, wherein the substrate comprises a transparent or translucent polymeric such that the reaction wells are formed in the sheet as a digital microfluidic array.

28. The apparatus of any preceding embodiment: wherein with a surface of each well is covered with nanoplasmonic structures; and wherein the light source configured to illuminate the nanoplasmonic structures on the surface of the wells at a resonance wavelength of nanoplasmonic structures and duration that causes plasmonic photothermal heating of the nanoplasmonic structures.

29. The apparatus of any preceding embodiment, wherein the control module is configured to control the light source for ultrafast thermal cycling for portable multiplexed PCR at low power consumption.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

Materials Parameters For Electromagnetic Simulation

| | Density $\rho$(kg m$^{-3}$) | Heat Capacity C.(J kg$^{-1}$ K$^{-1}$) | Thermal Conductivity k(W m$^{-1}$ K$^{-1}$) |
|---|---|---|---|
| Gold | 19,300 | 129 | 317 |
| PMMA | 1,180 | 1,420 | 1.93 |
| Water | 998 | 4,180 | 0.6 |

TABLE 2

Temperature As A Function Of Film Thickness And Injection Current

| | Thickness (nm) | | | | | | | | | |
|---|---|---|---|---|---|---|---|---|---|---|
| | 10 nm | | 20 nm | | 40 nm | | 80 nm | | 120 nm | |
| Current (mA) | Mean | Std. | Mean | Std. | Mean | Std. | Mean | Std. | Mean | Std. |
| 100 | 35.8 | 0.71 | 37.8 | 1.13 | 40.7 | 0.72 | 45.1 | 0.66 | 45.7 | .53 |
| 200 | 47.3 | 1.41 | 51.6 | 1.33 | 55.5 | 1.70 | 65.7 | 1.14 | 66.0 | 0.73 |
| 300 | 58.8 | 2.47 | 64.3 | 1.79 | 74.4 | 1.03 | 84.0 | 1.34 | 84.5 | 1.22 |
| 400 | 69.0 | 3.89 | 75.9 | 2.54 | 89.3 | 1.74 | 101.9 | 2.26 | 102.6 | 2.71 |
| 500 | 78.4 | 4.07 | 86.8 | 3.03 | 103.1 | 3.91 | 116.8 | 1.06 | 119.5 | 1.61 |
| 600 | 87.1 | 5.13 | 97.4 | 3.98 | 115.1 | 3.15 | 126.9 | 1.39 | 128.3 | 2.47 |
| 700 | 95.4 | 5.13 | 108.9 | 4.34 | 123.9 | 3.57 | 133.7 | 3.07 | 134.9 | 3.70 |
| 800 | 104.5 | 4.24 | 117.4 | 5.27 | 131.8 | 5.14 | 139.7 | 4.50 | 139.7 | 4.58 |
| 900 | 111.9 | 3.36 | 124.1 | 6.00 | 137.2 | 5.38 | 145.3 | 4.17 | 145.8 | 5.83 |
| 1000 | 118.9 | 4.77 | 128.1 | 5.84 | 142.0 | 5.29 | 150.1 | 4.20 | 151.5 | 5.29 |

What is claimed is:

1. An apparatus for nucleic acids amplification, comprising:
   a support platform comprising a plurality of arrays of wells, wherein each of the wells comprises a bottom surface bounded by one or more side walls and is configured to hold a sample;
   a film disposed within each of the wells, wherein for each well, the film is disposed on the bottom surface bounded by the one or more side walls;
   a substrate disposed below the support platform; and
   a plurality of light sources disposed on the substrate, wherein each light source of the plurality of light sources is configured to illuminate one array of wells of the plurality of arrays of wells with a beam of light such that the beam of light from each light source generates light-to-heat conversion within the film and subsequent heating of the sample, wherein each light source of the plurality of light sources is configured to be modulated separately such that each array of wells is characterized by a different annealing temperature.

2. The apparatus of claim 1, further comprising:
   a plurality of lenses disposed between the plurality of light sources and the support platform;
   wherein lens of the plurality of lenses is configured to focus the beam of light from one of the light sources at one of the arrays of wells.

3. The apparatus of claim 1, further comprising a temperature sensor configured to monitor a temperature of the sample.

4. The apparatus of claim 3, further comprising:
   a controller coupled to one or more of the plurality of light sources or the temperature sensor;
   wherein the controller is configured for controlling one or more of data acquisition from the temperature sensor or actuation of the one or more light sources of the plurality of light sources.

5. The apparatus of claim 4, wherein the controller is configured for controlling actuation of the one or more light sources of the plurality of light sources to modify one or more of exposure duration or injection current at the film.

6. The apparatus of claim 1, wherein the film comprises a nanometer sized grain to enhance light absorption through surface plasmon resonance.

7. The apparatus of claim 1, wherein the support platform comprises a translucent or transparent polymer.

8. The apparatus of claim 1, wherein the film comprises at least one of gold and platinum.

9. The apparatus of claim 2, further comprising a diffuser associated with each lens of the plurality of lenses to evenly distribute the beam of light to the film.

10. The apparatus of claim 1, wherein each light source of the plurality of light sources comprises an LED having a wavelength selected for maximum light absorption within the film.

11. The apparatus of claim 1, further comprising:
a digital camera, photodiode or spectrophotometer configured to perform real-time detection of nucleic acids within the sample.

12. A heater apparatus for nucleic acids amplification, the heater apparatus comprising:
a substrate support platform having a plurality of arrays of reaction wells, each reaction well having a bottom surface bounded by one or more side walls configured for holding a sample;
wherein an interior surface of each of the reaction wells is covered with a film disposed on the interior surface of each reaction well;
a substrate disposed below the support platform; and
a plurality of light sources disposed on the substrate, wherein each light source of the plurality of light sources is configured to concurrently illuminate an entirety of the film within one array of reaction wells of the plurality of arrays of reaction wells at a wavelength and duration that causes photothermal heating of the film and subsequent heating of the sample, wherein each light source of the plurality of light sources is configured to be modulated separately such that each array of reaction wells is characterized by a different annealing temperature.

13. The heater apparatus of claim 12, further comprising:
at least one temperature sensor configured to monitor the temperature of the sample in each of the reaction wells.

14. The heater apparatus of claim 13, further comprising:
(a) a control module coupled to the temperature sensor and each light source of the plurality of light sources;
(b) the control module comprising a processor and a memory storing instructions executable on the processor;
(c) said instructions, when executed by the processor, performing steps comprising:
(i) monitoring sample temperature; and
(ii) actuating each light source of the plurality of light sources at a frequency and duration to produce selected sample temperatures over time.

15. The heater apparatus of claim 14, wherein said instructions when executed by the processor further perform steps comprising detecting a fluorescence signal within the sample.

16. The heater apparatus of claim 12, wherein the support platform comprises a transparent or translucent polymer such that the reaction wells are formed in the film as a digital microfluidic array.

17. The heater apparatus of claim 16:
wherein a surface of each reaction well is covered with nanoplasmonic structures; and
wherein each light source of the plurality of light sources is configured to illuminate the nanoplasmonic structures on the surface of each of the reaction wells of a corresponding one of the plurality of arrays of reaction wells at a resonance wavelength of nanoplasmonic structures and duration that causes plasmonic photothermal heating of the nanoplasmonic structures.

18. The heater apparatus of claim 14, wherein the control module is configured to control each light source of the plurality of light sources to increase a rate of thermal cycling for multiplexed PCR to minimize power consumption.

19. The apparatus of claim 1, wherein each light source of the plurality of light sources comprises a light-emitting diode.

20. The apparatus of claim 1, wherein each light source of the plurality of light sources comprises a laser.

21. The heater apparatus of claim 12, wherein each light source of the plurality of light sources comprises a light emitting diode.

22. The heater apparatus of claim 12, wherein each light source of the plurality of light sources comprises a laser.

23. The apparatus of claim 1, wherein each film has a thickness of 10 nm to 120 nm.

24. The apparatus of claim 23, wherein the thickness is 40 nm.

* * * * *